(12) United States Patent
McDonald et al.

(10) Patent No.: US 7,696,204 B2
(45) Date of Patent: Apr. 13, 2010

(54) PHARMACEUTICAL COMPOUNDS

(75) Inventors: Edward McDonald, Surrey (GB); Jonathan M Large, Surrey (GB); Stephen J Shuttleworth, Berkshire (GB)

(73) Assignees: Ludwig Institute for Cancer Research, Zurich (CH); Cancer Research Technology Limited, London (GB); The Institute of Cancer Research: Royal Cancer Hospital, London (GB); Astellas Pharma, Inc., Tokyo (JP); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 12/089,677

(22) PCT Filed: Oct. 11, 2006

(86) PCT No.: PCT/GB2006/003782

§ 371 (c)(1),
(2), (4) Date: Aug. 22, 2008

(87) PCT Pub. No.: WO2007/042810

PCT Pub. Date: Apr. 19, 2007

(65) Prior Publication Data

US 2009/0042884 A1    Feb. 12, 2009

(30) Foreign Application Priority Data

Oct. 11, 2005    (GB) .................................. 0520657.8

(51) Int. Cl.
*C07D 239/48* (2006.01)
*A61K 31/505* (2006.01)

(52) U.S. Cl. ..................... 514/235.8; 544/122; 544/123

(58) Field of Classification Search ................. 544/122, 544/123; 514/235.8
See application file for complete search history.

(56) References Cited

U.S. PATENT DOCUMENTS 6,756,360 B1    6/2004    Erion et al.

FOREIGN PATENT DOCUMENTS

| WO | WO 99/19305 A | 4/1999 |
|---|---|---|
| WO | WO 02/47690 A1 | 6/2002 |
| WO | WO 02/88101 A2 | 11/2002 |
| WO | WO 02/102313 A1 | 12/2002 |
| WO | WO 03/32994 A | 4/2003 |
| WO | 2004/048365 | 6/2004 |
| WO | 2005/000404 | 1/2005 |
| WO | WO 2006/005914 A1 | 1/2006 |
| WO | WO 2006/005915 A1 | 1/2006 |
| WO | WO 2006/005918 A1 | 1/2006 |
| WO | WO 2006/034473 A | 3/2006 |
| WO | 2007/042806 | 4/2007 |
| WO | WO 2007/066103 A1 | 6/2007 |

OTHER PUBLICATIONS

Fry, Phosphoinoditide 3-Kinase signalling in breast cancer: how big a role might it play?, Breast Cancer Research, vol. 3, No. 5, pp. 304-312, 2001.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Douglas, Jr., Introduction to Viral Diseases, Cecil Textbook of Medicine, 20th Edition, vol. 2, pp. 1739-1742, 1996.*
Simone, Oncology: Introduction, Cecil Textbook of Medicine, 20th Edition, vol. 1, pp. 1004-1010, 1996.*
International Search Report for International Application No. PCT/GB2006/003782, mailed Dec. 19, 2006.
Written Opinion of the International Searching Authority, mailed Dec. 19, 2006.
M. Whitman et al, 1988, Nature, 332, 644-646.
B. Vanhaesebroeck et al, 1997, Trends in Biochemical Sciences, 22, 267-272.

* cited by examiner

*Primary Examiner*—Deepak Rao
(74) *Attorney, Agent, or Firm*—Nixon & Vanderhye P.C.

(57) ABSTRACT

Pyrimidines of formula (I):

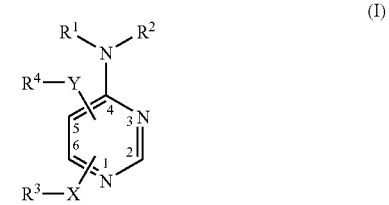

wherein $R^1$ to $R^4$, X and Y are defined in the specification are inhibitors of P13K and may thus be used to treat diseases and disorders arising from abnormal cell growth, function or behavior associated with P13 kinase such as cancer, immune disorders, cardiovascular disease, viral infection, inflammation, metabolism/endocrine function disorders and neurological disorders.

7 Claims, No Drawings

_US 7,696,204 B2_

PHARMACEUTICAL COMPOUNDS

This application is the U.S. national phase of International Application No. PCT/GB2006/003782, filed 11 Oct. 2006, which designated the U.S. and claims priority to GB 0520657.8, filed 11 Oct. 2005, the entire contents of each of which are hereby incorporated by reference.

FIELD OF THE INVENTION

The present invention relates to pyrimidine compounds and to their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (M. Whitman et al, 1988, Nature, 332, 644-646).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck et al, 1997, _Trends in Biochemical Sciences_, 22, 267-262). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3 K and which suppress cancer cell growth.

SUMMARY OF THE INVENTION

It has now been found that a series of novel pyrimidine compounds have activity as inhibitors of PI3K. The compounds exhibit selectivity for class Ia PI3Ks over class Ib, in particular for the p110δ subtype. Accordingly, the present invention provides a compound which is a pyrimidine of formula (I):

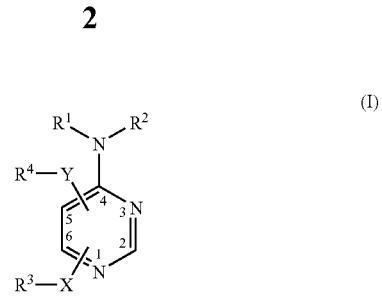

wherein
—XR$^3$ is bonded at ring position 2 and —YR$^4$ is bonded at ring position 5 or 6, or —YR$^4$ is bonded at ring position 2 and —XR$^3$ is bonded at ring position 6;

R$^1$ and R$^2$ form, together with the N atom to which they are attached, a morpholine ring which is unsubstituted or substituted;

X is selected from a direct bond, —O—, —CR'R"— and —NR'— wherein R' and R" are each, independently, H or C$_1$-C$_6$ alkyl;

R$^3$ is an indole group which is unsubstituted or substituted; and either:

(a) Y is selected from —O—(CH$_2$)$_n$—, —NH—(CH$_2$)$_n$—, —NHC(O)—(CH$_2$)$_n$— and —C(O)NH—(CH$_2$)$_n$— wherein n is 0 or an integer of 1 to 3, and R$^4$ is selected from an unsaturated 5- to 12-membered carbocyclic or heterocyclic group which is unsubstituted or substituted and a group —NR$^5$R$^6$ wherein R$^5$ and R$^6$, which are the same or different, are each independently selected from H, C$_1$-C$_6$ alkyl which is unsubstituted or substituted, C$_3$-C$_{10}$ cycloalkyl which is unsubstituted or substituted, —C(O)R, —C(O)N(R)$_2$ and —S(O)$_m$R wherein R and m are as defined above, or R$^5$ and R$^6$ together form, with the nitrogen atom to which they are attached, a saturated 5-, 6- or 7-membered N-containing heterocyclic group which is unsubstituted or substituted;

(b) Y is a direct bond and R$^4$ is selected from an unsaturated 5- to 12-membered carbocyclic or heterocyclic group which is unsubstituted or substituted, and a group —NR$^5$R$^6$ wherein R$^5$ and R$^6$, which are the same or different, are each independently selected from H, C$_1$-C$_6$ alkyl which is unsubstituted or substituted, C$_3$-C$_{10}$ cycloalkyl which is unsubstituted or substituted, —C(O)R, —C(O)N(R)$_2$ and —S(O)$_m$R wherein R and m are as defined above;

or a pharmaceutically acceptable salt thereof.

The invention also provides a compound which is a pyrimidine of formula (I'):

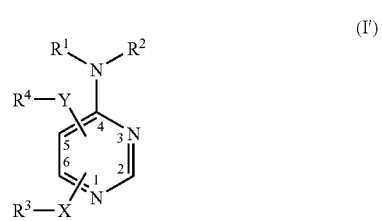

wherein
P —XR$^3$ is bonded at ring position 2 and —YR$^4$ is bonded at ring position 5 or 6, or —YR$^4$ is bonded at ring position 2 and —XR$^3$ is bonded at ring position 6;

R$^1$ and R$^2$, which are the same or different, are each independently selected from H, C$_1$-C$_6$ alkyl which is unsubstituted or substituted, C$_3$-C$_{10}$ cycloalkyl which is unsubstituted or substituted, and $C_1$-$C_6$ alkoxy which is unsubstituted or substituted, or $R^1$ and $R^2$ form, together with the N atom to which they are attached, a saturated 5-, 6- or 7-membered N-containing heterocyclic ring which includes 0, 1 or 2 additional heteroatoms selected from O, N and S and which is unsubstituted or substituted;

X is selected from a direct bond, —O—, —CR'R"— and —NR'— wherein R' and R" are each, independently, H or $C_1$-$C_6$ alkyl;

$R^3$ is selected from:

(i) a group of the following formula:

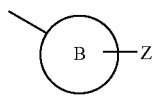

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —$C(O)N(R)_2$, —$NR_2$, —$NRC(O)R$, —$S(O)_m$ $N(R)_2$, —$OC(O)R$, $OC(O)N(R)_2$, —$NRS(O)_mR$, —$NRC(O)N(R)_2$, CN, halogen and —$NO_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;

(ii) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (iii) a group comprising a benzene ring which is unsubstituted or substituted and which is fused to a heteroaryl group as defined above; and either:

(a) Y is selected from —O—$(CH_2)_n$—, —NH—$(CH_2)_n$—, —NHC(O)—$(CH_2)_n$— and —C(O)NH—$(CH_2)_n$— wherein n is 0 or an integer of 1 to 3, and $R^4$ is selected from an unsaturated 5- to 12-membered carbocyclic or heterocyclic group which is unsubstituted or substituted and a group —$NR^5R^6$ wherein $R^5$ and $R^6$, which are the same or different, are each independently selected from H, $C_1$-$C_6$ alkyl which is unsubstituted or substituted, $C_3$-$C_{10}$ cycloalkyl which is unsubstituted or substituted, —C(O)R, —C(O)N(R)$_2$ and —S(O)$_m$R wherein R and m are as defined above, or $R^5$ and $R^6$ together form, with the nitrogen atom to which they are attached, a saturated 5-, 6- or 7-membered N-containing heterocyclic group which is unsubstituted or substituted;

(b) Y is a direct bond and $R^4$ is selected from an unsaturated 5- to 12-membered carbocyclic or heterocyclic group which is unsubstituted or substituted, and a group —$NR^5R^6$ wherein $R^5$ and $R^6$, which are the same or different, are each independently selected from H, $C_1$-$C_6$ alkyl which is unsubstituted or substituted, $C_3$-$C_{10}$ cycloalkyl which is unsubstituted or substituted, —C(O)R, —C(O)N(R)$_2$ and —S(O)$_m$R wherein R and m are as defined above;

or a pharmaceutically acceptable salt thereof.

DETAILED DESCRIPTION OF THE INVENTION

A $C_1$-$C_6$ alkyl group is linear or branched. A $C_1$-$C_6$ alkyl group is typically a $C_1$-$C_4$ alkyl group, for example a methyl, ethyl, propyl, n-butyl, sec-butyl or tert-butyl group. A $C_1$-$C_6$ alkyl group is unsubstituted or substituted, typically by one or more groups Z as defined above, or by one or more groups Z as defined above or $R^7$ as defined below. Typically it is $C_1$-$C_4$ alkyl, for example methyl, ethyl, i-propyl, n-propyl, t-butyl, s-butyl or n-butyl.

$R^7$ is selected from $C_1$-$C_6$ alkoxy, $OR^8$, $SR^8$, $S(O)_mR^8$, nitro, CN, halogen, —$C(O)R^8$, —$CO_2R^8$, —$C(O)N(R^8)_2$ and —$N(R^8)_2$, wherein each $R^8$, which are the same or different when more than one is present in a given substituent, is selected from H, $C_1$-$C_6$ alkyl and $C_3$-$C_{10}$ cycloalkyl., and m is 1 or 2.

A halogen is F, Cl, Br or I. Preferably it is F, Cl or Br. A $C_1$-$C_6$ alkyl group substituted by halogen may be denoted by the term "halo-$C_1$-$C_6$ alkyl", which means an alkyl group in which one or more hydrogens is replaced by halo. A halo-$C_1$-$C_6$ alkyl group preferably contains one, two or three halo groups. A preferred example of such a group is trifluoromethyl.

A $C_1$-$C_6$ alkoxy group is linear or branched. It is typically a $C_1$-$C_4$ alkoxy group, for example a methoxy, ethoxy, propoxy, i-propoxy, n-propoxy, n-butoxy, sec-butoxy or tert-butoxy group. A $C_1$-$C_6$ alkoxy group is unsubstituted or substituted, typically by one or more groups Z or $R^7$ as defined above.

A $C_3$-$C_{10}$ cycloalkyl group may be, for instance, $C_3$-$C_8$ cycloalkyl such as cyclopropyl, cyclobutyl, cyclopentyl, cyclohexyl, or cycloheptyl. Typically it is $C_3$-$C_6$ cycloalkyl. A $C_3$-$C_{10}$ cycloalkyl group is unsubstituted or substituted, typically by one or more groups Z or $R^7$ as defined above.

A $C_1$-$C_6$ acyl group is a group —C(O)Alk in which Alk is $C_1$-$C_6$ alkyl as defined above. It is, for instance, formyl, acetyl or propionyl.

A saturated 5-, 6-, or 7-membered N-containing heterocyclic ring may be, for example, piperidine, piperazine, morpholine or pyrrolidine. The ring typically contains one nitrogen atom and either an additional N atom or an O atom, or no additional heteroatoms. The ring is unsubstituted or substituted on one or more ring carbon atoms and/or on any additional N atom present in the ring. Examples of suitable substituents include one or more groups Z or $R^7$ as defined above, and a $C_1$-$C_6$ alkyl group which is unsubstituted or substituted by a group Z or $R^7$ as defined above. When the ring is piperazine it is typically unsubstituted or substituted, typically on the second ring nitrogen atom, by —$C(O)R^8$, —$C(O)N(R^8)_2$ or —$S(O)_mR^8$, or by $C_1$-$C_6$ alkyl which is unsubstituted or substituted by $C_1$-$C_6$ alkoxy or OH.

An unsaturated 5- to 12-membered carbocyclic group is a 5-, 6-, 7-, 8-, 9-, 10, 11- or 12-membered carbocyclic ring containing at least one unsaturated bond. It is a monocyclic or fused bicyclic ring system. The group is aromatic or non-aromatic, for instance a 5- to 12-membered aryl group. Examples include phenyl, naphthyl, indanyl, indenyl and tetrahydronaphthyl groups. The group is unsubstituted or substituted, typically by one or more groups Z or $R^7$ as defined above.

An aryl group is a 5- to 12-membered aromatic carbocyclic group. It is monocyclic or bicyclic. Examples include phenyl and naphthyl groups. The group is unsubstituted or substituted, for instance by a group Z or $R^7$ as defined above.

An unsaturated 5- to 12-membered heterocyclic group is typically heteroaryl. Heteroaryl is a 5- to 12-membered heteroaryl group which contains 1, 2, 3, or 4 heteroatoms selected from O, N and S. Typically it contains one N atom and 0, 1, 2 or 3 additional heteroatoms selected from O, S and N. It may be, for example, furan, thiophene, pyrrole, indole, isoindole, pyrazole, imidazole, benzothiophene, benzothiazole, benzofuran, isoxazole, oxazole, oxadiazole, thiazole, isothiazole, thiadiazole, dihydroimidizole, pyridine, pyridine, quinoline, isoquinoline, quinoxaline, thianopyrazine, pyran, pyrimidine, pyridazine, pyrazine, triazine, triazole or tetrazole. The group is unsubstituted or substituted, typically by one or more groups Z or $R^7$ as defined above. In the definition of $R^4$ this heterocyclic group is typically selected from pyridine, thiophene and pyrrole. Most typically it is pyridine, for instance a pyrid-2-yl, pyrid-3-yl or pyrid-4-yl group.

In formula (I') $R^1$ and $R^2$ typically form, together with the N atom to which they are attached, a secondary or tertiary amine, most typically a tertiary amine. The amine is acyclic or cyclic. Thus, one or both of $R^1$ and $R^2$ is typically a $C_1$-$C_6$ alkyl group which is unsubstituted or substituted. If the alkyl group is substituted it is typically substituted by Z or $R^7$ as defined above. When $R^1$ or $R^2$ is a $C_1$-$C_6$ alkyl group which is unsubstituted it is typically a methyl or ethyl group. When $R^1$ or $R^2$ is a $C_1$-$C_6$ alkyl group which is substituted it is typically $C_1$-$C_6$ alkyl substituted by a group selected from $C_1$-$C_6$ alkoxy and —$NR_2$ as defined above, for instance $C_1$-$C_6$ alkyl substituted by —$OCH_3$ or by —$NH_2$, —$NHCH_3$ or —$N(CH_3)_2$. Thus one or both of $R^1$ and $R^2$ may be —$(CH_2)_r$—$OR^{13}$ wherein r is 0 or an integer of 1 to 6, for instance 1 to 4, such as 1, 2, 3 or 4, and $R^{13}$ is $C_1$-$C_6$ alkyl. Alternatively one or both of $R^1$ and $R^2$ may be —$(CH_2)_r$—$NR_2$ wherein r and R are as defined above. Typically one or each of $R^1$ and $R^2$ is selected from —$(CH_2)_2OCH_3$, —$(CH_2)_2NH_2$, —$(CH_2)_2NHCH_3$ and —$(CH_2)_2N(CH_3)_2$.

In formula (I) $R^1$ and $R^2$ form, together with the N-atom to which they are attached, a morpholine ring. The ring is unsubstituted or substituted, either on a ring carbon atom or (if present) on a second heteroatom, for instance by a group Z or $R^7$ as defined above.

In formula (I), in the definition of $R^3$, the indole group is linked to the pyrimidine ring via any available ring C or N atom. For instance, it is an indol-4-yl, indol-5-yl or indol-6-yl group. Typically it is an indol-4-yl or indol-6-yl group.

In formula (I'), in the definition (i) for $R^3$, the phenyl ring B is unsubstituted (apart from group Z) or substituted. When it is unsubstituted the group Z is the sole substituent. When it is substituted it typically comprises, in addition to group Z, one or more substituents selected from halo, alkyl, alkenyl, alkynyl, CN, NO$_2$, OR', SR', NR'$_2$, C(O)R', SOR', SO$_2$R', SO$_2$NR'$_2$, NC(O)R' and CO$_2$R', wherein each R' is independently H or $C_1$-$C_6$ alkyl. Group Z is bonded to any available ring position on the phenyl ring B. Typically the phenyl ring, which is otherwise unsubstituted or substituted, for instance as specified above, is meta-substituted or para-substituted by Z. Thus it may be situated at the 2-, 3-, 4-, 5- or 6- position of the phenyl ring.

Typically it is bonded at position 3 or 4. Z is most typically other than H, such that moiety -BZ is a substituted phenyl ring. A typical example of Z is a group OR as defined above, in particular OH. In this embodiment the OR group, or OH group, is typically bonded at ring position 3 or 4 of phenyl ring B. Typically -BZ is a 3-hydroxyphenyl or 4-hydroxyphenyl group, or an isostere thereof.

An isostere as used herein is a functional group which possesses binding properties which are the same as, or similar to, the 3-hydroxyphenyl or 4-hydroxyphenyl group in the context of the structure of formula (I). An indole group is an isostere of 3-hydroxyphenyl and 4-hydroxyphenyl groups. In the definition for $R^3$ in formula (I) the indole group is unsubstituted or substituted. If it is substituted it may be substituted by one or more substituents selected from a group Z or $R^7$ as defined above, any group specified above as an additional substituent on the phenyl ring B, and an oxo group (=O).

Typically, if substituted, the heteroaryl group is substituted by OH, NH$_2$ or an oxo group. In one embodiment the heteroaryl group is unsubstituted.

In formula (I'), in definition (iii) for $R^3$, the benzene ring is unsubstituted or substituted. If it is substituted it may be substituted by a group Z or $R^7$ as defined above or by any of the groups specified above as options an additional substituent on the phenyl ring B. The heteroaryl group to which the benzene ring is fused is itself unsubstituted or substituted, for instance by a group Z or $R^7$ as defined above, by any group specified above as an option for an additional substituent on the phenyl ring B, or by an oxo group (=O). In one embodiment both the benzene ring and the heteroaryl group are unsubstituted.

Examples of the groups included in definitions (ii) and (iii) for $R^3$ in formula (I) include pyrrole, pyrazole, triazole, tetrazole, indazole, thiazole, isothiazole, oxazole, isoxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance as specified above.

When $R^4$ is an unsaturated 5- to 12-membered carbocyclic group it is typically an aromatic carbocyclic group such as phenyl or naphthyl. When $R^4$ is an unsaturated 5- to 12-membered heterocyclic group it is typically pyridyl, for instance a pyrid-2-yl, pyrid-3-yl or pyrid-4-yl group. When $R^4$ is a saturated 5-, 6- or 7- membered N-containing heterocyclic group it is typically a 6-membered such heterocyclic group, for instance piperidyl or morpholinyl. The group $R^4$ is unsubstituted or substituted, for instance by a group Z or $R^7$ as defined above.

The linker group X in formula (I) is typically a direct bond, —O—, —CH$_2$—, —CHR$^{13}$—, —NH— or —NR$^{13}$ wherein $R^{13}$ is $C_1$-$C_6$ alkyl. Most typically it is a direct bond.

In one embodiment the pyrimidine is of formula (Ia):

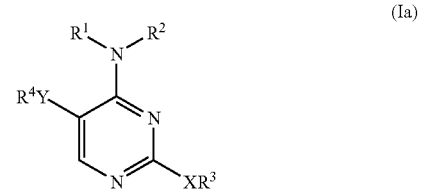

(Ia)

wherein $R^1$, $R^2$, $R^3$, $R^4$, X and Y are as defined above for formula (I).

In formula (Ia) Y is typically —NH—C(O)— or C(O)—NH—; $R^4$ is typically an aromatic unsaturated 5- to 12-membered carbocyclic or heterocyclic group which is unsubstituted or substituted, for instance a phenyl or pyridyl group. The pyridyl group may be a pyrid-2-yl, pyrid-3-yl or pyrid-4-yl group. XR$^3$ is an indole group. Typically XR$^3$ is an indol-4-yl or indol-6-yl group, more typically an indol-4-yl group. $R^1$ and $R^2$ form, together with the N atom to which they are attached, a morpholino group.

In a second embodiment the pyrimidine is of formula (Ib):

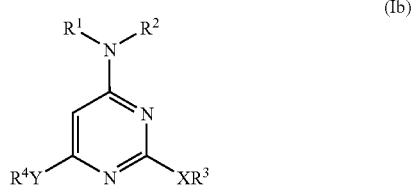

wherein $R^1$, $R^2$, $R^3$, $R^4$, Y and X are as defined above for formula (I).

In formula (Ib), Y is typically a direct bond or a group —O—$(CH_2)_n$— in which n is 1 or 2 and $R^4$ is an aromatic unsaturated 5- to 12-membered carbocyclic or heterocyclic group which is unsubstituted or substituted, for instance a phenyl or pyridyl group. The phenyl group is unsubstituted or substituted, for instance by a group Z or a group $R^7$ as defined above, for example by a halogen such as Cl or Br. The pyridyl group is unsubstituted or substituted by a group Z or $R^7$ as defined above. Alternatively Y may be a group —NH—$(CH_2)_n$— in which n is 1 or 2 and $R^4$ may be an aromatic unsaturated 5- to 12-membered carbocyclic or heterocyclic group or a group —$NR^5R^6$ as defined above, for instance a group —$NR^5R^6$ wherein $R^5$ and $R^6$ form, together with the nitrogen atom to which they are attached, a saturated 5-, 6- or 7-membered N-containing heterocyclic group. Typically $R^4$ is an unsubstituted pyrid-2-yl, pyrid-3-yl or pyrid-4-yl group, or a piperidine or morpholine group. $R^1$ and $R^2$ preferably form, together with the N atom to which they are attached, a morpholino group.

In a third embodiment the pyrimidine is of formula (Ic):

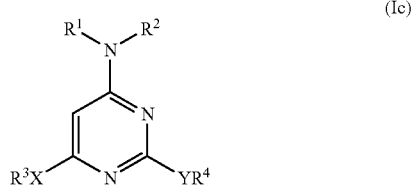

wherein $R^1$, $R^2$, $R^3$, $R^4$, Y and X are as defined above for formula (I).

In formula (Ic), Y may be a group —NH—$(CH_2)_n$— in which n is 1 or 2 and $R^4$ may be an aromatic unsaturated 5- to 12-membered carbocyclic or heterocyclic group or a group —$NR^5R^6$ as defined above, for instance a group —$NR^5R^6$ wherein $R^5$ and $R^6$ form, together with the N atom to which they are attached, a saturated 5-, 6- or 7-membered N-containing heterocyclic group such as a piperidine or morpholine group. Typically $R^4$ is an unsubstituted pyrid-2-yl, pyrid-3-yl or pyrid-4-yl group, or a piperidine or morpholine group. Alternatively Y may be a group —O—$(CH_2)_n$— in which n is 1 or 2 and $R^4$ may be an aromatic unsaturated 5- to 12-membered carbocyclic or heterocyclic group which is unsubstituted or substituted, for instance an pyrid-2-yl, pyrid-3-yl or pyrid-4-yl group.

Specific examples of compounds of the invention include:
6-(indol-4-yl)-4-(morpholin-4-yl)-2-[(2-(pyridin-2-yl)ethylamino]pyrimidine;
2-(indol-4-yl)-4-(morpholin-4-yl)-6-[(2-(pyridin-2-yl)ethylamino]pyrimidine;
6-(indol-4-yl)-4-(morpholin-4-yl)-2-[(2-(pyridin-3-yl)ethylamino]pyrimidine;
2-(indol-4-yl)-4-(morpholin-4-yl)-6-[(2-(pyridin-3-yl)ethylamino]pyrimidine;
6-(indol-4-yl)-4-(morpholin-4-yl)-2-[(2-(pyridin-4-yl)ethylamino]pyrimidine;
2-(indol-4-yl)-4-(morpholin-4-yl)-6-[(2-(pyridin-4-yl)ethylamino]pyrimidine;
2-(indol-4-yl)-4-(morpholin-4-yl)-6-(pyridin-2-ylmethyloxy)pyrimidine;
6-(indol-4-yl)-4-(morpholin-4-yl)-2-(pyridin-2-ylmethyloxy)pyrimidine;
6-(indol-6-yl)-4-(morpholin-4-yl)-2-[(2-(pyridin-2-yl)ethylamino]pyrimidine;
2-(indol-6-yl)-4-(morpholin-4-yl)-6-[(2-(pyridin-2-yl)ethylamino]pyrimidine;
6-(indol-6-yl)-4-(morpholin-4-yl)-2-[(2-(pyridin-3-yl)ethylamino]pyrimidine;
2-(indol-6-yl)-4-(morpholin-4-yl)-6-[(2-(pyridin-3-yl)ethylamino]pyrimidine;
6-(indol-6-yl)-4-(morpholin-4-yl)-2-[(2-(pyridin-4-yl)ethylamino]pyrimidine;
2-(indol-6-yl)-4-(morpholin-4-yl)-6-[(2-(pyridin-4-yl)ethylamino]pyrimidine;
2-(indol-6-yl)-4-(morpholin-4-yl)-6-(pyridin-2-ylmethyloxy)pyrimidine;
6-(indol-6-yl)-4-(morpholin-4-yl)-2-(pyridin-2-ylmethyloxy)pyrimidine.

and the pharmaceutically acceptable salts thereof.

Pyrimidines of formula (I) may be converted into pharmaceutically acceptable salts, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds of the invention bearing a free carboxy substituent, the salts include both the above-mentioned acid addition salts and the salts of sodium, potassium, calcium and ammonium. The latter are prepared by treating the free pyrimidine of formula (I), or the acid addition salt thereof, with the corresponding metal base or ammonia.

The pyrimidines of formula (I) may be prepared by any suitable synthetic route, for instance selected from those set out in any of schemes 1 to 8 below.

Scheme 1

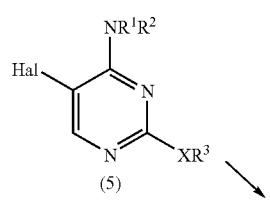

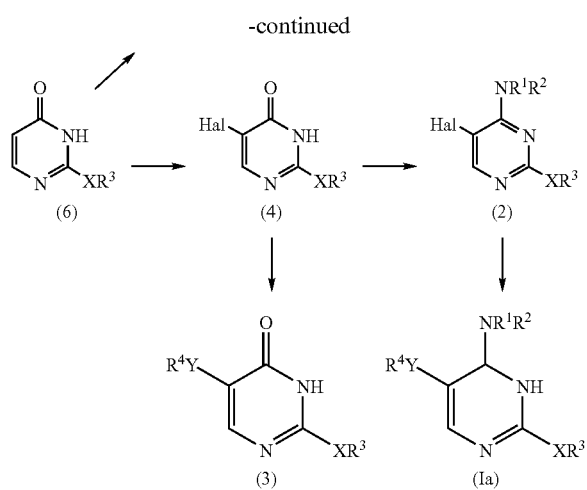

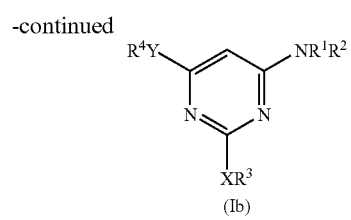

In scheme 1, $R^1$, $R^2$, $R^3$, $R^4$, X and Y are as defined above for formula (I) and Hal is a halogen. Compounds of formula (Ia) may be prepared by the Suzuki coupling of a compound of formula (2) with a boronic acid $R^4Y$—$B(OH)_2$ (Y is a to direct bond) in the presence of Pd (0) and a base, for instance using the general procedure described in Reference Example 15 which follows. A compound of formula (2) may be prepared by treating a compound of formula (5) with a halogen ($Cl_2$, $Br_2$, $I_2$) or a source of halogen (N-chlorosuccinimide, N-bromosuccinimide or N-iodosuccinimide) in an inert solvent. A compound of formula (5) may be prepared from a compound of formula (6) by treatment with phosphorous oxychloride in the presence of an N, N-dialkylaniline, followed by treatment with an amine of formula $NHR^1R^2$ in an inert solvent in the presence of a base. A compound of formula (4) may be prepared by treating a compound of formula (6) with a halogen in the presence of an acid.

A compound of formula (I) may alternatively be prepared by treating a compound of formula (3) with phosphorous oxychloride in the presence of an N, N-dialkylaniline, followed by treatment with an amine of formula $NHR^1R^2$ in an inert solvent in the presence of a base. A compound of formula (3) may be prepared by the Suzuki coupling of a compound of formula (4) with a boronic acid of formula $R^4Y$—$B(OH)_2$ (Y is a direct bond) in the presence of Pd (0) and a base.

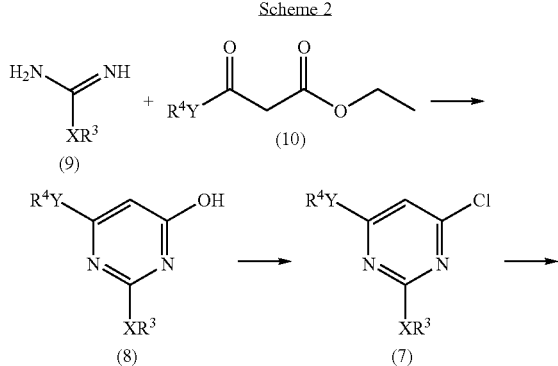

In scheme 2, $R^1$, $R^2$, $R^3$, $R^4$, X and Y are as defined above for formula (I). Compounds of formula (Ib) may be prepared by treating compounds of formula (7) with an amine of formula $HNR^1R^2$ in an inert solvent in the presence of a base. Compounds of formula (7) may be prepared by treating compounds of formula (8) with phosphorous oxychloride in the presence of an N, N-dialkylaniline. Compounds of formula (8) may be prepared by reacting together compounds of formula (9) and (10) in an inert solvent.

Compounds of formula (10) were prepared according to the method in *Tetrahedron*, 1991, 47, 975. Compounds of formula (9) were prepared according to *J. Med. Chem.*, 1995, 38, 2251.

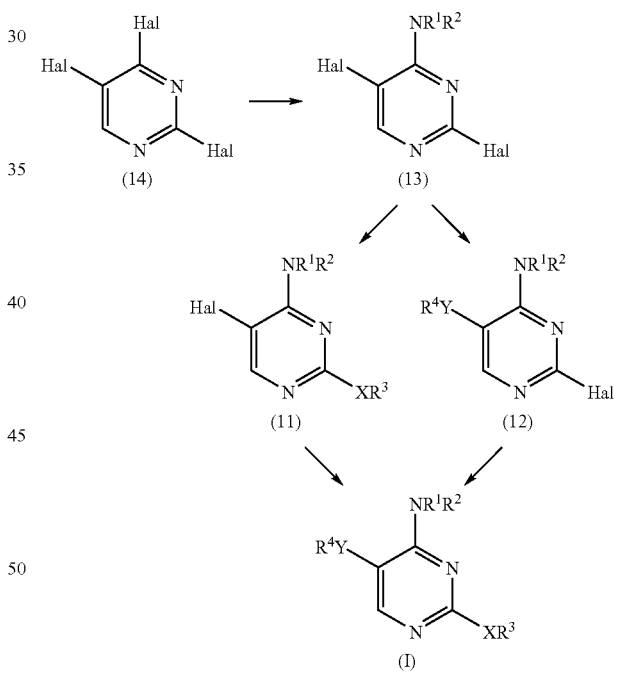

In scheme 3, $R^1$, $R^2$, $R^3$, $R^4$, X and Y are as defined above for formula (I). Compounds of formula (I) may be prepared by the Suzuki coupling of either a compound of formula (12) with a boronic acid of formula $R^3X$—$B(OH)_2$, or a compound of formula (11) with a boronic acid of formula $R^4Y$—$B(OH)_2$, in the presence of Pd and a base. Compounds of formulae (11) and (12) may be prepared by the Suzuki coupling of a compound of formula (13) with, respectively, a boronic acid of formula $R^3X$—$B(OH)_2$ or a boronic acid of formula $R^4Y$—$B(OH)_2$, in each case in the presence of Pd and a base. A compound of formula (13) may be prepared by treating a solution of a compound of formula (14) with an amine of formula HNR$^1$R$^2$ in the presence of a base. The trihalopyrimidines of formula (14) are known compounds and may be obtained commercially or synthesized by known methods.

When R$^3$ in the end product is an indolyl group, the required indole boronic acid of formula R$^3$X—B(OH)$_2$ may be prepared by treating the corresponding brominated indole group with an alkyl lithium base followed by quenching with a trialkylborate. Alternatively, indole boronic acid compounds are commercially available.

R$^4$—OH(Y is —O—(CH$_2$)$_n$— wherein n is 0) or an amine R$^4$—NH$_2$ (Y is —NH—(CH$_2$)$_n$— wherein n is 0) gives compounds of formula (1b). Compounds of formula (11) may be prepared by treating compounds of formula (52) with one molar equivalent of an amine of formula HNR$^1$R$^2$ in an inert solvent in the presence of a base. Compounds of formula (52) may be prepared by treating compounds of formula (53) with phosphorous oxychloride in the presence of an N, N-dialkylaniline. Compounds of formula (53) may be prepared by reacting together compounds of formula (9) and (54) in an inert solvent in the presence of a base.

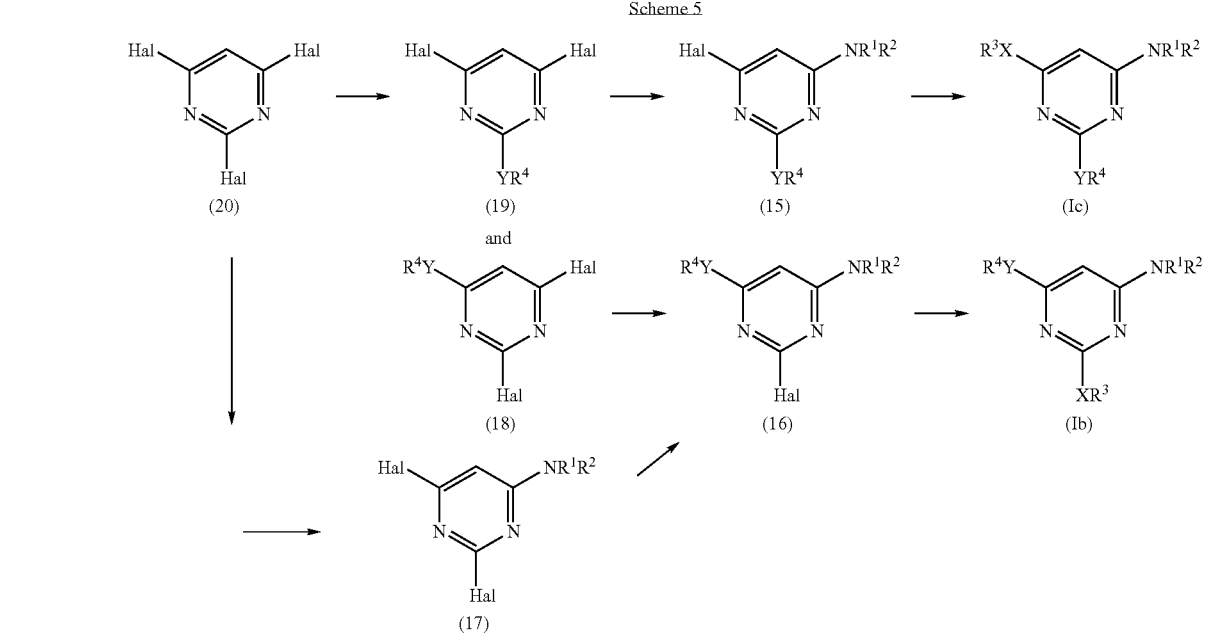

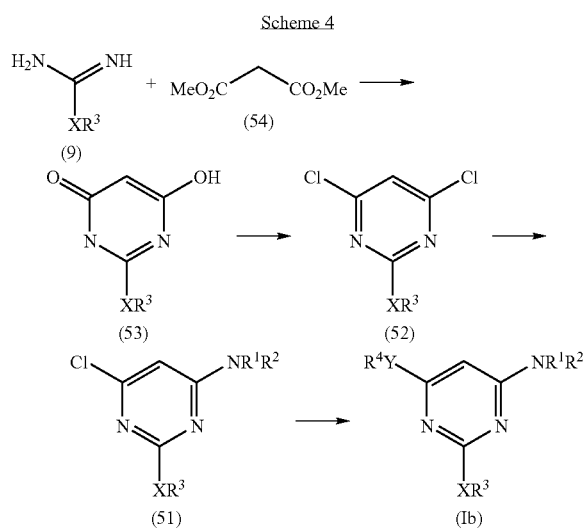

In Scheme 4, R$^1$, R$^2$, R$^3$, R$^4$ and X are as defined above for formula (I). Treatment of (51) with either a boronic acid R$^4$—B(OH)$_2$ (Y is a direct bond), a suitable alcohol In Scheme 5, R$^1$, R$^2$, R$^3$, R$^4$, Y and X are as defined above for formula (I), and Hal is a halogen. Compounds of formula (1b) or (1c) may be prepared by Suzuki coupling of compounds of formula (15) or (16) respectively with a boronic acid R$^3$X—B(OH)$_2$ in the presence of Pd (0) and a base, for instance using the general procedure described in Reference Example 15. A compound of formula (15) may be prepared by treatment of a compound of formula (19) with one molar equivalent of an amine of formula HNR$^1$R$^2$ in an inert solvent in the presence of a base at room temperature. A compound of formula (16) may be obtained by treatment of a compound of formula (18) with two molar equivalents of an amine of formula HNR$^1$R$^2$ in an inert solvent at elevated temperature (for example 80° C.).

The isomeric compounds (18) and (19) can both be prepared by treating a compound of formula (20) with either a boronic acid R$^4$—B(OH)$_2$ (Y is a direct bond), a suitable alcohol R$^4$—OH(Y is —O—(CH$_2$)$_n$— wherein n is 0) or an amine R$^4$—NH$_2$ (Y is —NH—(CH$_2$)$_n$— wherein n is 0) and separating the two products.

Alternatively a compound of formula (16) may be prepared by treatment of a compound of formula (17) with either a boronic acid R$^4$—B(OH)$_2$ (Y is a direct bond), a suitable alcohol R$^4$—OH(Y is —O—(CH$_2$)$_n$— wherein n is 0) or an amine R$^4$—NH$_2$ (Y is —NH—(CH$_2$)$_n$— wherein n is 0). A compound of formula (17) may be prepared by treatment of a compound of formula (20) with one molar equivalent of an amine of formula HNR$^1$R$^2$ in an inert solvent in the presence of a base. Compounds of formulae (19) and (18) were prepared as described in Reference Example 3.

When R$^3$ in the end product is an indolyl group, the required indole boronic acid of formula R$^3$X—B(OH)$_2$ may be prepared by treating the corresponding brominated indole with an alkyl lithium base followed by quenching with a trialkylborate. Alternatively, an indole boronic acid may be obtained commercially.

A compound (1b) or (1c) in which X is other than a direct bond may be prepared by treating the intermediate (16) or (15), respectively, with a suitable amine, alcohol or thiol nucleophile under neutral or basic conditions.

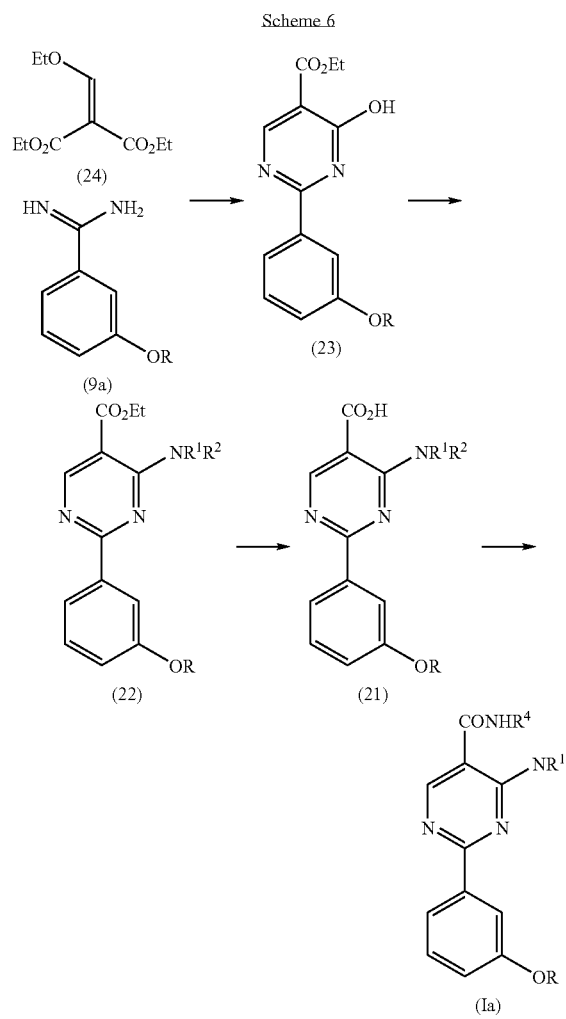

In Scheme 6, R$^1$, R$^2$, R$^4$ and OR are as defined above for formula (I) OR being one option for R$^3$ in formula (I)). Compounds of formula (Ia) can be prepared by coupling of an acid of structure (21) with an amine by one of the standard methods of amide bond formation. Compounds like (21) can be obtained by hydrolysis of esters of type (22). Structures like (22) can be obtained from compounds of formula (23) by treatment with phosphorous oxychloride in the presence of an N, N-dialkylaniline, followed by treatment with an amine of formula NHR$^1$R$^2$ in an inert solvent in the presence of a base. Compounds like (23) can be obtained by reacting together compounds of formula (9a) with commercially available compound (24) in an inert solvent. Compounds (23), (22) and (21) can be prepared as described in Reference Examples 7 to 9 which follow.

An indole analogue of the end product of formula (Ia), in which the OR-substituted phenyl group is replaced by an indole group, may be prepared according to scheme 6 by replacing the amidine compound (9a) by a corresponding amidine in which the OR-substituted phenyl group is replaced by an indole group. The amidine in this case may be prepared, for instance, by the addition of ammonia or a synthetic equivalent thereof to the corresponding indole nitrile, followed by acidic work up.

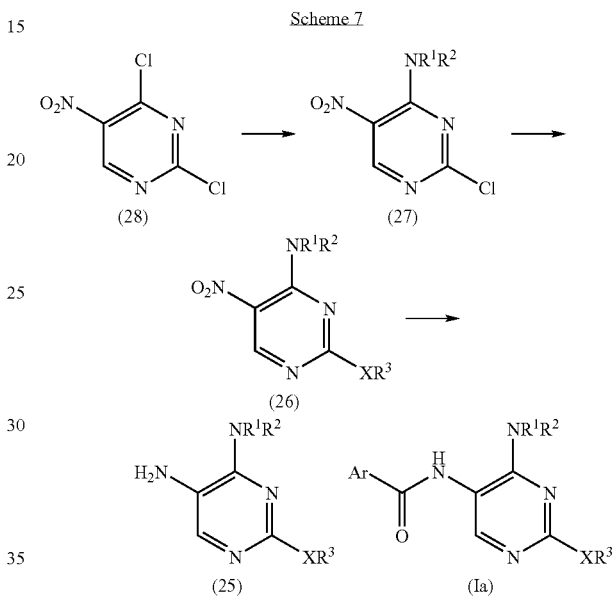

In scheme 7, R$^1$, R$^2$, R$^3$ and X are as defined for formula (I) and Ar is an unsaturated 5- to 12-membered carbocyclic or heterocyclic group which is unsubstituted or substituted, as defined above within the definition of R$^4$ in formula (I). Compounds of formula (I) can be prepared by the reaction of a compound of formula (25) with an acid chloride in the presence of a base in an inert solvent. A compound of formula (25) can be prepared by reduction of a compound of formula (26), using for example catalytic hydrogenation over a suitable metal catalyst. A compound of formula (26) may be prepared by Suzuki coupling of compounds of formula (27) with a boronic acid R$^3$X—B(OH)$_2$ in the presence of Pd (0) and a base. Compounds of formula (27) can be prepared by treatment of compound (28) with an amine of formula NHR$^1$R$^2$ in an inert solvent in the presence of a base. Compound (28) can be prepared by treatment of commercially available 5-nitrouracil with phosphorous oxychloride in the presence of an N, N-dialkylaniline.

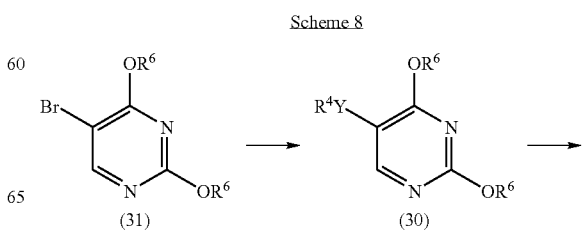

-continued

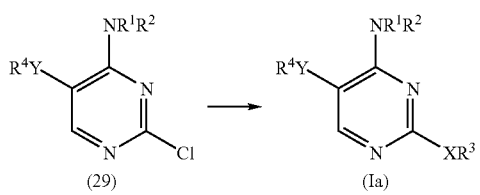

In scheme 8, $R^1$, $R^2$, $R^3$, $R^4$, X and Y are as defined above for formula (I) and $R^6$ is linear or branched $C_1$-$C_4$ alkyl or $SiR^7R^8R^9$ wherein each of $R^7$, $R^8$ and $R^9$, which are the same or different, is linear or branched $C_1$-$C_4$ alkyl, or phenyl. Compounds of formula (1a) may be prepared by Suzuki coupling of compounds of formula (29) with a boronic acid $R^3X$—$B(OH)_2$ in the presence of Pd (0) and a base, for instance using the general procedure described in Reference Example 15. A compound of formula (29) may be prepared by treatment of a compound of formula (30) with phosphorous oxychloride in the presence of an N, N-dialkylaniline, followed by treatment with an amine of formula $NHR^1R^2$ in an inert solvent in the presence of a base. Compounds like (30) could be prepared by coupling of compounds of type (31) with for example a boronic acid $R^3X$—$B(OH)_2$.

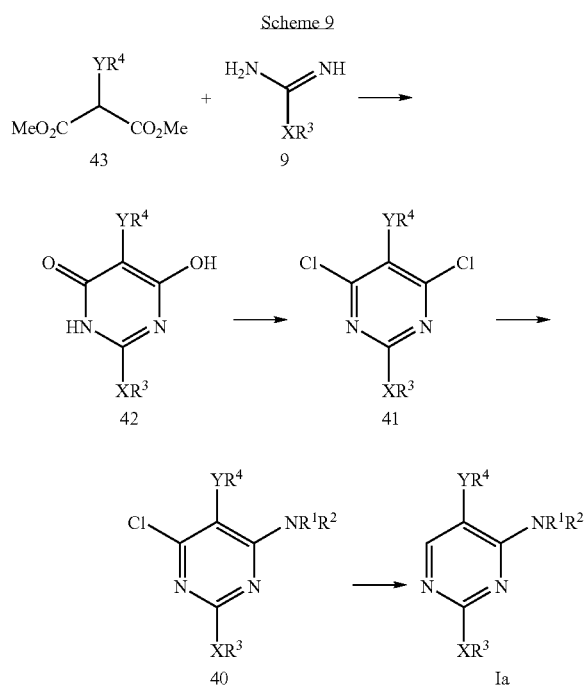

In scheme 9, $R^1$, $R^2$, $R^3$, $R^4$, X and Y are as defined above for formula (I). Compounds of formula 1a may be prepared by treatment of a compound of formula 40 with a suitable reducing agent (eg. hydrogen). A compound of formula 40 may be prepared by treatment of a compound of formula 41 with an amine of formula $NHR^1R^2$ in an inert solvent in the presence of a base. A compound of formula 41 may be prepared from a compound of formula 42 by treatment with phosphorous oxychloride in the presence of an N,N-dialkylaniline. Compounds of formula 42 may be prepared by reacting together compounds of formula 9 and 43 in an inert solvent in the presence of a base. Compounds of formula 43 may be prepared from commercially available dimethyl halomalonate compounds (where halo refers to chloro, bromo or iodo) by means of suitable nucleophilic displacement reactions.

Compounds of the present invention have been found in biological tests to be inhibitors of PI3 kinase. The compounds are selective for class Ia PI3 kinases over class Ib and typically exhibit at least a 20-fold selectivity for class Ia over class Ib PI3 kinases. In general the compounds are selective for the p110δ isoform over p110γ.

A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase. Examples of such diseases and disorders are discussed by Drees et al in Expert Opin. Ther. Patents (2004) 14(5): 703-732. These include proliferative disorders such as cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas.

A compound of the present invention may be used as an inhibitor of PI3 kinase. A human or animal patient suffering from a disease or disorder arising from abnormal cell growth, function or behaviour associated with PI3 kinase, such as an immune disorder, cancer, cardiovascular disease, viral infection, inflammation, a metabolism/endocrine disorder or a neurological disorder, may thus be treated by a method comprising the administration thereto of a compound of the present invention as defined above. The condition of the patient may thereby be improved or ameliorated.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight, A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolize to glucose or which only metabolize a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

The invention will be further described in the Examples which follow:

REFERENCE EXAMPLE 1

Preparation of Intermediates (18) and (19) in Scheme 5

2,4-dichloro-6-(pyridin-2-ylmethylamino)pyrimidine (L1) and 4,6-dichloro-2-(pyridin-2-ylmethylamino)pyrimidine (M1)

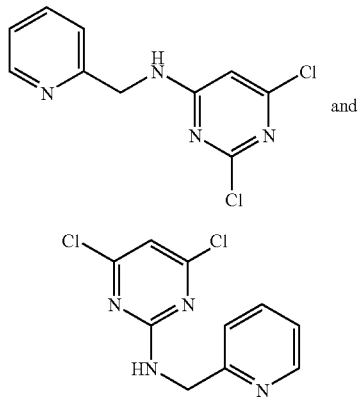

A solution of 2,4,6-trichloropyrimidine (1.00 g, 5.45 mmol) in dioxane (15 ml) at room temperature was treated with diisopropylethylamine (1.1 eq, 6.00 mmol, 1.04 ml) and dropwise with 2-aminomethylpyridine (1.1 eq, 6.00 mmol, 0.62 ml) and stirred for 2 h. tlc analysis (EtOAc-hexane, 3:1) showed conversion to 2 products. The dioxane was evaporated in vacuo, and the residue partitioned between $H_2O$ (15 ml) and $CHCl_3$ (15 ml). The organic layer was separated and the aqueous layer further extracted with $CHCl_3$ (2×10 ml). The combined extracts were dried ($Na_2SO_4$) and concentrated in vacuo. Purification by column chromatography (same eluent) gave the product L1 (575 mg, 41%) and the 2-isomer M1 (280 mg, 20%) as pale yellow solids.

L1: $\delta_H$ (250 MHz, $CDCl_3$) 8.49 (1H, d, J 4.5, pyridine Ar), 7.66 (1H, td, J 7.5, 1.5, pyridine Ar), 7.25-7.17 (2H, m, 2× pyridine Ar), 6.85 (1H, br, NH), 6.36 (1H, s, br, pyrimidine Ar), 4.66 (2H, br, $CH_2$).

M1: $\delta_H$ (250 MHz, $CDCl_3$) 8.49 (1H, d, J 4.5, pyridine Ar), 7.61 (1H, td, J 7.5, 1.5, pyridine Ar), 7.24-7.12 (2H, m, 2× pyridine Ar), 6.71 (1H, br, NH), 6.56 (1H, s, pyrimidine Ar), 4.66 (2H, d, J 5.0, $CH_2$).

Examples of further compounds of formula (18) that were prepared using this method are as follows:

2,4-dichloro-6-(pyridin-3-ylmethylamino)pyrimidine (N1)

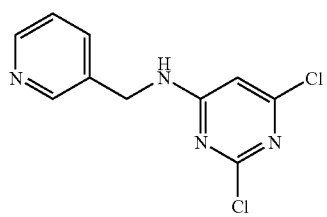

$\delta_H$ (250 MHz, $CDCl_3$) 8.50 (2H, m, 2× pyridine Ar), 7.62 (1H, d, J 7.5, pyridine Ar), 7.28-7.25 (1H, m, pyridine Ar), 6.26 (1H, s, pyrimidine Ar), 5.95 (1H, br, NH), 4.58 (2H, br, $CH_2$).

2,4-dichloro-6-[(2-(pyridin-2-yl)ethylamino]pyrimidine (O1)

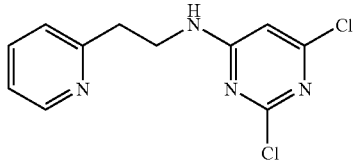

$\delta_H$ (250 MHz, $CDCl_3$) 8.55 (1H, d, J 4.0, pyridine Ar), 7.66 (1H, td, J 7.5, 2.0, pyridine Ar), 7.23-7.19 (2H, m, 2× pyridine Ar), 6.66 (1H, br, NH), 6.31 (1H, s, pyrimidine Ar), 3.92-3.85 (2H, m, $NHCH_2$), 3.12 (2H, t, 16.0, $ArCH_2$).

2,4-dichloro-6-[2-(pyridin-3-yl)ethylamino]pyrimidine (P1)

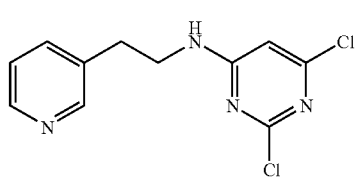

$\delta_H$ (250 MHz, $CDCl_3$) 8.41-8.37 (1H, m, pyridine Ar), 7.48 (2H, d, J 8.0, pyridine Ar), 7.20 (1H, t, J 6.0, pyridine Ar), 6.20 (1H, s, pyrimidine Ar), 5.75 (1H, br, NH), 3.63-3.61 (2H, m, $NHCH_2$), 2.88 (2H, t, J 7.0, $ArCH_2$).

2,4-dichloro-6-[2-(pyridin-4-yl)ethylamino]pyrimidine (Q1)

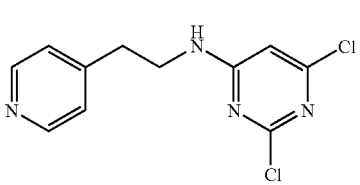

$\delta_H$ (250 MHz, $CDCl_3$) 8.47 (2H, d, J 6.0, 2× pyridine Ar), 7.08 (2H, d, J 6.0, 2× pyridine Ar), 6.20 (1H, s, pyrimidine Ar), 5.28 (1H, br, NH), 3.62 (2H, s, br, $NHCH_2$), 2.87 (2H, t, J 7.0, $ArCH_2$).

2,4-dichloro-6-[2-(morpholin-4-yl)ethylamino]pyrimidine (R1)

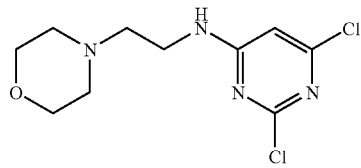

4,6-dichloro-2-(pyridin-4-ylmethylamino)pyrimidine (U1)

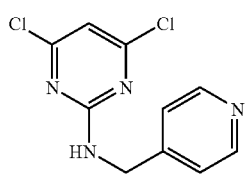

$\delta_H$ (250 MHz, CDCl$_3$) 6.21 (1H, br s, pyrimidine Ar), 5.97 (1H, br, NH), 3.63-3.60 (4H, m, 2× morpholine CH$_2$), 3.41-3.31 (2H, m, br, NHCH$_2$), 2.51 (2H, t, J 6.0, ArCH$_2$), 2.40-2.37 (4H, m, 2× morpholine CH$_2$).

$\delta_H$ (250 MHz, CDCl$_3$) 8.49 (2H, d, J 6.0, 2× pyridine Ar), 7.17 (2H, d, J 6.0, 2× pyridine Ar), 6.60 (1H, s, pyrimidine Ar), 6.24 (1H, br, NH), 4.61 (2H, d, J 6.5, CH$_2$).

4,6-dichloro-2-[(2-(pyridin-2-yl)ethylamino]pyrimidine (V1)

2,4-dichloro-6-[2-piperidin-1-yl)ethylamino]pyrimidine (S1)

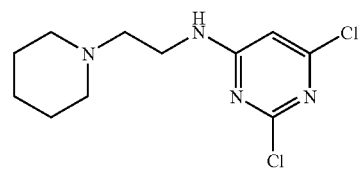

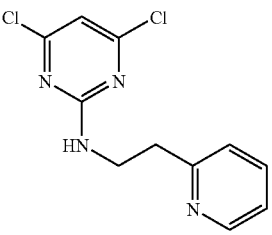

$\delta_H$ (250 MHz, CDCl$_3$) 6.21 (1H, br s, pyrimidine Ar), 6.05 (1H, br, NH, 3.39 (1H, br, q, J 5.0, NHCH$_A$H$_B$), 3.15 (1H, br, NHCH$_A$H$_B$), 2.47 (2H, t, J 6.0, NCH$_2$), 2.32-2.30 (4H, br, 2× piperidine CH$_2$), 1.55-1.48 (4H, m, 2× piperidine CH$_2$), 1.40-1.38 (2H, m, piperidine CH$_2$).

Examples of compounds of formula (19) that were prepared using this method are as follows:

$\delta_H$ (250 MHz, CDCl$_3$) 8.48 (1H, d, J 6.0, pyridine Ar), 7.54 (1H, td, J 7.5, 2.0, pyridine Ar), 7.11-7.06 (2H, m, 2× pyridine Ar), 6.50 (1H, s, pyrimidine Ar), 6.20 (1H, br, NH), 3.80 (2H, q, J 6.0, NHCH$_2$), 3.01 (2H, t, J 6.0, ArCH$_2$).

4,6-dichloro-2-[2-(pyridin-3-yl)ethylamino]pyrimidine (W1)

4,6-dichloro-2-(pyridin-3-ylmethylamino)pyrimidine (T1)

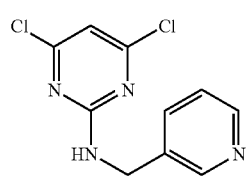

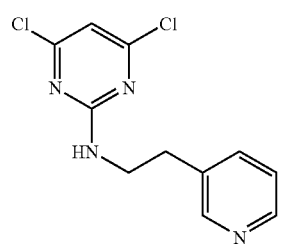

$\delta_H$ (250 MHz, CDCl$_3$) 8.55 (1H, d, J 2.0, pyridine Ar), 8.47 (1H, dd, J 5.0, 1.5, pyridine Ar), 7.61 (1H, dd, J 8.0, 2.0, pyridine Ar), 7.24-7.20 (1H, m, pyridine Ar), 6.59 (1H, s, pyrimidine Ar), 6.06 (1H, br, NH), 4.59 (2H, d, J 6.0, CH$_2$).

$\delta_H$ (250 MHz, CDCl$_3$) 8.43 (2H, m, 2× pyridine Ar), 7.50 (1H, dt, J 7.5, 2.0, pyridine Ar), 7.21-7.16 (1H, m, pyridine Ar), 6.55 (1H, s, pyrimidine Ar), 5.48 (1H, br, NH), 3.64 (2H, q, J 7.0, NHCH$_2$), 2.85 (2H, q, J 7.0, ArCH$_2$).

4,6-dichloro-2-[2-(pyridin-4-yl)ethylamino]pyrimidine (X1)

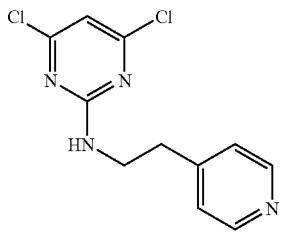

$\delta_H$ (250 MHz, CDCl$_3$) 8.46 (2H, dd, J 4.5, 1.5, 2× pyridine Ar), 7.09 (2H, dd, J 4.5, 1.5, 2× pyridine Ar), 6.55 (1H, s, pyrimidine Ar), 5.54 (1H, br, NH), 3.66 (2H, q, J 7.0, NHCH$_2$), 2.84 (2H, t, J 7.0, ArCH$_2$).

4,6-dichloro-2-[2-(morpholin-4-yl)ethylamino]pyrimidine (Y1)

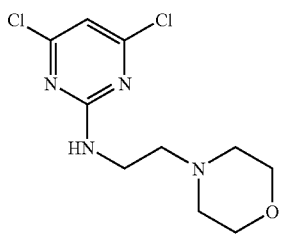

$\delta_H$ (250 MHz, CDCl$_3$) 6.52 (1H, s, pyrimidine Ar), 6.00 (1H, br, NH), 3.66-3.62 (4H, m, 2× morpholine CH$_2$), 3.43 (2H, q, J 6.0, NHCH$_2$), 2.50 (2H, t, J 6.0, NCH$_2$), 2.43-2.39 (4H, m, 2× morpholine CH$_2$).

4,6-dichloro-2-[2-piperidin-1-yl)ethylamino]pyrimidine (Z1)

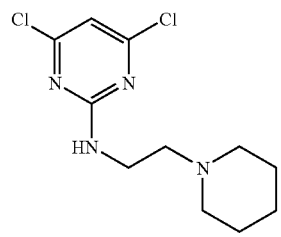

$\delta_H$ (250 MHz, CDCl$_3$) 6.50 (1H, s, pyrimidine Ar), 6.12 (1H, br, NH), 3.40 (2H, q, J 5.5, NHCH$_2$), 2.44 (2H, t, J 6.0, NCH$_2$), 2.33-2.31 (4H, m, 2× piperidine CH$_2$), 1.54-1.46 (4H, m, 2× piperidine CH$_2$), 1.41-1.37 (2H, m, 1× piperidine CH$_2$).

REFERENCE EXAMPLE 2

Preparation of Further Intermediates (18) and (19) in Scheme 5

4,6-dichloro-2-(pyridin-2-ylmethyloxy)pyrimidine (A2) and 2,4-dichloro-6-(pyridin-2-ylmethyloxy)pyrimidine (B2)

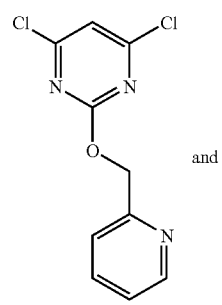

and

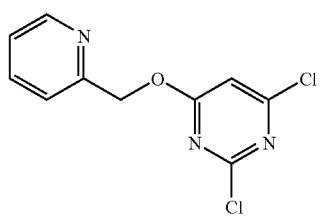

Compounds A2 and B2 were prepared according to the method described in WO 99/65881, as follows:

248 mg of NaH (60% in mineral oil, 10.36 mmol) was added to a solution of 2-pyridinemethanol (0.90 eq, 9.81 mmol, 0.95 ml) in THF (20 ml) at room temperature and stirred for 30 minutes. After cooling to −78° C., 2,4,6-trichloropyrimidine (2 g, 10.90 mmol) was added dropwise and the reaction allowed to warm to room temperature and stirred for 3 h. Saturated aqueous NH$_4$Cl (20 ml) was added and the mixture extracted with EtOAc (20 ml). The organic phase was dried (MgSO$_4$) and evaporated in vacuo. Column chromatography (EtOAc-DCM, 1:1) gave a mixture of the two products (491 mg, 18%) as a pale yellow solid and in a ratio of 2.4:1, with compound B2 tentatively assigned as the major isomer; $\delta_H$ (250 MHz, CDCl$_3$) 8.66-8.61 (2H, m, 1× pyridine Ar major, 1× pyridine Ar minor), 7.75 (1H, td, J 8.0, 2.0, 1× pyridine Ar major), 7.74 (1H, td, J 8.0, 2.0, 1× pyridine Ar minor), 7.53 (1H, d, J 8.0, 1× pyridine Ar minor), 7.44 (1H, d, J 8.0, 1× pyridine Ar major), 7.32-7.24 (2H, m, 1× pyridine Ar major, 1× pyridine Ar minor), 7.09 (1H, s, pyrimidine Ar minor), 6.84 (1H, s, pyrimidine Ar major), 5.59 (2H, s, CH$_2$ minor), 5.58 (2H, s, CH$_2$ major).

REFERENCE EXAMPLE 3

Preparation of Intermediates (15) in Scheme 5

6-chloro-4-(morpholin-4-yl)-2-(pyridin-2-ylmethylamino)pyrimidine (C2)

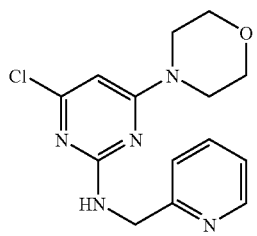

A solution of compound M1 (100 mg, 0.39 mmol) in dioxane (1 ml) at room temperature was treated with diisopropylethylamine (1.5 eq, 0.59 mmol, 0.10 ml) and morpholine (1.5 eq, 0.59 mmol, 0.05 ml) and stirred at room temperature for 2 h. tlc analysis (EtOAc) then showed complete conversion. The dioxane was evaporated in vacuo, and the residue partitioned between $H_2O$ (5 ml) and $CHCl_3$ (5 ml). The organic layer was separated and the aqueous layer further extracted with $CHCl_3$ (2×2 ml). The combined extracts were dried ($Na_2SO_4$) and concentrated in vacuo. Purification by column chromatography (same eluent) gave the product (101 mg, 83%) as a colourless solid; $\delta_H$ (250 MHz, $CDCl_3$) 8.47 (1H, d, J 4.0, pyridine Ar), 7.56 (1H, td, J 7.5, 2.0, pyridine Ar), 7.24-7.20 (1H, m, pyridine Ar), 7.09 (1H, dd, J 7.5, 5.0, pyridine Ar), 6.07 (1H, br, NH), 5.81 (1H, s, pyrimidine Ar), 4.62 (2H, d, J 5.5, $NHCH_2$), 3.67-3.60 (4H, m, 2× morpholine $CH_2$), 3.46-3.42 (4H, m, 2× morpholine $CH_2$).

Using an analogous method the following further compounds (15) were prepared:

6-chloro-4-(morpholin-4-yl)-2-(pyridin-3-ylmethylamino)pyrimidine (D2)

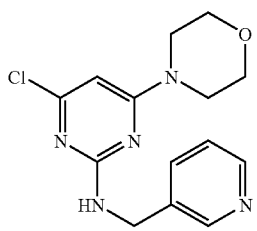

D2

$\delta_H$ (250 MHz, $CDCl_3$) 8.52 (1H, s, pyridine Ar), 8.43 (1H, d, J 4.0, pyridine Ar), 7.58 (1H, d, J 8.0, pyridine Ar), 7.18-7.15 (1H, m, pyridine Ar), 5.83 (1H, s, pyrimidine Ar), 5.61 (1H, br, NH), 4.52 (2H, d, J 6.0, $NHCH_2$), 3.65-3.62 (4H, m, 2× morpholine $CH_2$), 3.46-3.42 (4H, m, 2× morpholine $CH_2$).

6-chloro-4-(morpholin-4-yl)-2-(pyridin-4-ylmethylamino)pyrimidine (E2)

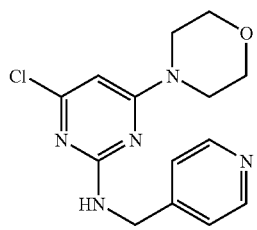

E2

$\delta_H$ (250 MHz, $CDCl_3$) 8.50 (2H, d, J 6.0, 2× pyridine Ar), 7.32 (2H, d, J 6.0, 2× pyridine Ar), 5.86 (1H, s, pyrimidine Ar), 5.52 (1H, br, NH), 4.57 (2H, d, J 6.0, $NHCH_2$), 3.64-3.60 (4H, m, 2× morpholine $CH_2$), 3.43-3.39 (4H, m, 2× morpholine $CH_2$).

6-chloro-4-(morpholin-4-yl)-2-[(2-(pyridin-2-yl)ethylamino]pyrimidine (F2)

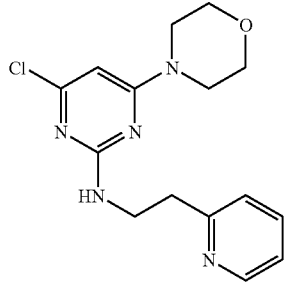

F2

$\delta_H$ (250 MHz, $CDCl_3$) 8.47 (1H, d, J 5.0, pyridine Ar), 7.52 (1H, td, J 7.5, 2.0, pyridine Ar), 7.09-7.04 (2H, m, 2× pyridine Ar), 5.77 (1H, s, pyrimidine Ar), 5.38 (1H, br t, J 5.0, NH), 3.78-3.65 (6H, m, 2× morpholine $CH_2$ and $NHCH_2$), 3.57-3.46 (4H, m, 2× morpholine $CH_2$), 2.98 (2H, t, J 6.5, $ArCH_2$).

6-chloro-4-(morpholin-4-yl)-2-[(2-(pyridin-3-yl)ethylamino]pyrimidine (G2)

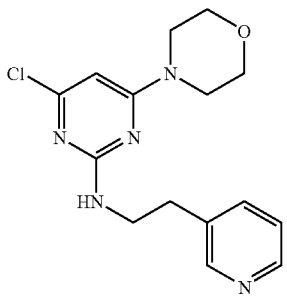

G2

$\delta_H$ (250 MHz, $CDCl_3$) 8.41-8.38 (2H, m, pyridine Ar), 7.45 (1H, d, J 7.5, pyridine Ar), 7.17-7.12 (1H, m, pyridine Ar), 5.80 (1H, s, pyrimidine Ar), 5.18 (1H, br, NH), 3.74-3.66 (4H, m, 2× morpholine $CH_2$), 3.56 (2H, q, J 7.0, $NHCH_2$), 3.50-3.41 (4H, m, 2× morpholine $CH_2$), 2.82 (2H, t, J 7.0, $ArCH_2$).

6-chloro-4-(morpholin-4-yl)-2-[(2-(pyridin-4-yl)ethylamino]pyrimidine (H2)

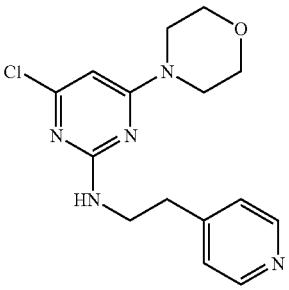

H2

$\delta_H$ (250 MHz, $CDCl_3$) 8.45 (2H, d, J 6.0, 2× pyridine Ar), 7.11 (2H, d, J 6.0, 2× pyridine Ar), 5.82 (1H, s, pyrimidine Ar), 4.98 (1H, br, NH), 3.70-3.66 (4H, m, 2× morpholine $CH_2$), 3.59 (2H, q, J 7.0, $NHCH_2$), 3.49 (4H, m, 2× morpholine $CH_2$), 2.83 (2H, t, J 7.0, $ArCH_2$).

6-chloro-4-(morpholin-4-yl)-2-[2-(morpholin-4-yl)ethylamino]pyrimidine

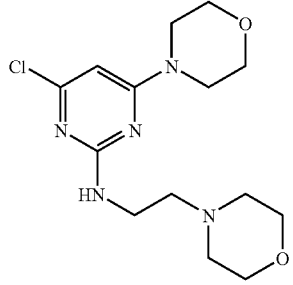

I2

$\delta_H$ (250 MHz, CDCl$_3$) 5.79 (1H, s, pyrimidine Ar), 5.45 (1H, br, NH), 3.69-3.58 (8H, m, 4× morpholine CH$_2$), 3.51-3.47 (4H, m, 2× morpholine CH$_2$), 3.39 (2H, q, J 6.0, NHCH$_2$), 2.49 (2H, t, J 6.0, NCH$_2$), 2.44-2.40 (4H, m, 2× morpholine CH$_2$).

6-chloro-4-(morpholin-4-yl)-2-(pyridin-2-ylmethyloxy)pyrimidine (J2)

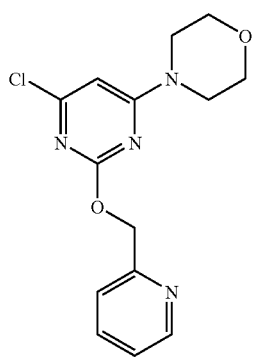

J2

$\delta_H$ (250 MHz, CDCl$_3$) 8.49 (1H, d, J 5.0, 1× pyridine Ar), 7.63 (1H, td, J 8.0, 2.0, 1× pyridine Ar), 7.44 (1H, d, J 8.0, 1× pyridine Ar), 7.14 (1H, dd, J 8.0, 5.0, 1× pyridine Ar), 6.11 (1H, s, pyrimidine Ar), 5.41 (2H, s, OCH$_2$), 3.68-3.64 (4H, m, 2× morpholine CH$_2$), 3.53-3.50 (4H, m, 2× morpholine CH$_2$).

REFERENCE EXAMPLE 4

Preparation of Intermediates (16) in Scheme 5

2-chloro-4-(morpholin-4-yl)-6-(pyridin-2-ylmethylamino)pyrimidine (K2)

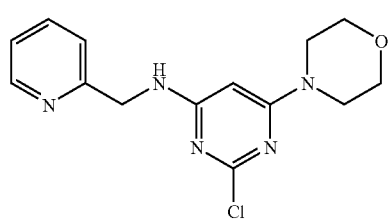

K2

A solution of compound L1 (100 mg, 0.39 mmol) in dioxane (1 ml) was treated with diisopropylethylamine (1.5 eq, 0.59 mmol, 0.10 ml) and morpholine (1.8 eq, 0.70 mmol, 0.06 ml) and heated to 70° C. for 8 hours. tlc analysis (CHCl$_3$-MeOH, 9:1) showed complete conversion. The dioxane was evaporated in vacuo, and the residue partitioned between H$_2$O (5 ml) and CHCl$_3$ (5 ml). The organic layer was separated and the aqueous layer further extracted with CHCl$_3$ (2×2 ml). The combined extracts were dried (Na$_2$SO$_4$) and concentrated in vacuo. Purification by column chromatography (same eluent) gave the product (91 mg, 76%) as a colourless solid; $\delta_H$ (250 MHz, CDCl$_3$) 8.49 (1H, d, J 4.5, pyridine Ar), 7.60 (1H, td, J 8.0, 2.0, pyridine Ar), 7.22-7.12 (2H, m, 2× pyridine Ar), 5.85 (1H, br, NH), 5.75 (1H, s, pyrimidine Ar), 4.56 (2H, d, J 5.0, NHCH$_2$), 3.68-3.60 (8H, m, 4× morpholine CH$_2$).

Using an analogous method the following further compounds (16) were prepared:

2-chloro-4-(morpholin-4-yl)-6-(pyridin-3-ylmethylamino)pyrimidine (L2)

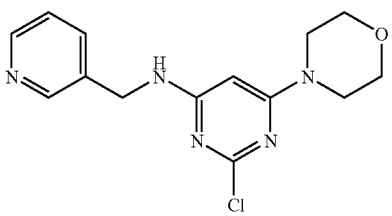

L2

$\delta_H$ (250 MHz, CDCl$_3$) 8.51 (1H, d, J 2.0, pyridine Ar), 8.46 (1H, dd, J 5.0, 1.5, pyridine Ar), 7.57 (1H, dd, J 8.0, 2.0, pyridine Ar), 7.23-7.18 (1H, m, pyridine Ar), 5.68 (1H, s, pyrimidine Ar), 5.03 (1H, br, NH), 4.49 (2H, d, J 6.0, NHCH$_2$), 3.68-3.60 (8H, m, 4× morpholine CH$_2$).

2-chloro-4-(morpholin-4-yl)-6-(pyridin-4-ylmethylamino)pyrimidine (M2)

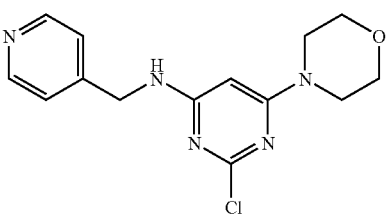

M2

$\delta_H$ (250 MHz, CDCl$_3$) 8.52 (2H, d, J 6.0, 2× pyridine Ar), 7.33 (2H, d, J 6.0, 2× pyridine Ar), 5.72 (1H, s, pyrimidine Ar), 5.36 (1H, br, NH), 4.57 (2H, d, J 6.0, NHCH$_2$), 3.65-3.55 (8H, m, 4× morpholine CH$_2$).

2-chloro-4-(morpholin-4-yl)-6-[(2-(pyridin-2-yl)ethylamino]pyrimidine (N2)

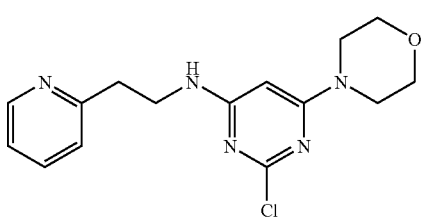

N2

$\delta_H$ (250 MHz, CDCl$_3$) 8.48 (1H, dt, J 5.0, 1.5 pyridine Ar), 7.55 (1H, td, J 7.5, 2.0, pyridine Ar), 7.12-7.07 (2H, m, 2× pyridine Ar), 5.64 (1H, s, pyrimidine Ar), 5.39 (1H, br, NH), 3.65-3.62 (10H, m, 4× morpholine CH$_2$, NHCH$_2$), 2.98 (2H, t, J 6.5, ArCH$_2$).

2-chloro-4-(morpholin-4-yl)-6-[(2-(pyridin-3-yl)ethylamino]pyrimidine (O2)

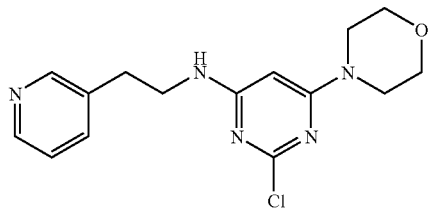

$\delta_H$ (250 MHz, CDCl$_3$) 8.44-8.39 (2H, m, 2× pyridine Ar), 7.45 (1H, dt, J 8.0, 2.0, pyridine Ar), 7.20-7.16 (1H, m, pyridine Ar), 5.62 (1H, s, pyrimidine Ar), 4.73 (1H, br, NH), 3.66 (8H, br s, 4× morpholine CH$_2$), 3.52 (2H, br q J 6.5, NHCH$_2$), 2.83 (2H, t J 7.0, ArCH$_2$).

2-chloro-4-(morpholin-4-yl)-6-[(2-(pyridin-4-yl)ethylamino]pyrimidine (P2)

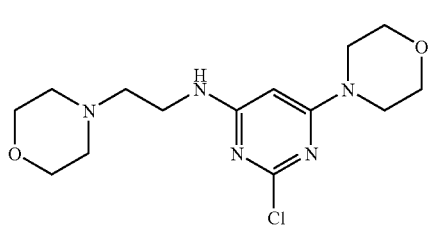

$\delta_H$ (250 MHz, CDCl$_3$) 8.58 (2H, d, J 6.0, 2× pyridine Ar), 7.24 (2H, d, J 6.0, 2× pyridine Ar), 5.74 (1H, s, pyrimidine Ar), 4.88 (1H, br, NH), 3.80-3.63 (10H, m, 4× morpholine CH$_2$, NHCH$_2$), 2.98 (2H, t, J 7.0, ArCH$_2$).

2-chloro-4-(morpholin-4-yl)-6-[2-(morpholin-4-yl)ethylamino]pyrimidine (Q2)

Q2

$\delta_H$ (250 MHz, CDCl$_3$) 5.67 (1H, s, pyrimidine Ar), 5.22 (1H, br, NH), 3.70-3.62 (12H, m, 6× morpholine CH$_2$), 3.30 (2H, br, NHCH$_2$), 2.50 (2H, t, J 6.0, NCH$_2$), 2.40 (4H, t, J 4.5, 1× morpholine CH$_2$).

2-chloro-4-(morpholin-4-yl)-6-(pyridin-2-ylmethyloxy)pyrimidine (R2)

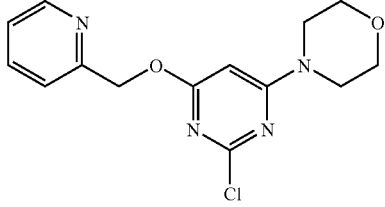

$\delta_H$ (250 MHz, CDCl$_3$) 8.51 (1H, d, J 4.5, 1× pyridine Ar), 7.63 (1H, td, J 8.0, 2.0, 1× pyridine Ar), 7.31 (1H, d, J 8.0, 1× pyridine Ar), 7.16 (1H, dd, J 7.0, 5.5, 1× pyridine Ar), 6.08 (1H, s, pyrimidine Ar), 5.40 (2H, s, OCH$_2$), 3.68-3.59 (8H, m, 4× morpholine CH$_2$).

REFERENCE EXAMPLE 5

Preparation of Intermediates (23) in Scheme 6

Ethyl 2-(3-benzyloxyphenyl)-4-hydroxypyrimidine carboxylate (H3)

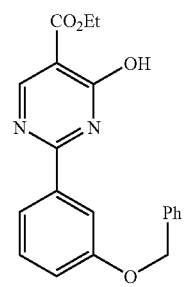

To a solution of the malonate derivative (24) 1.5 g, 6.95 mmol) and the amidine S (1.1 eq, 7.65 mmol, 1.73 g) in ethanol (20 ml) was added sodium ethoxide (1.1 eq, 7.65 mmol, 520 mg) and the mixture stirred at room temperature for 4 h. After this time, the solid product was filtered off and allowed to dry in air, affording 1.56 g (64%) as a pale yellow solid; $\delta_H$ (250 MHz, DMSO-d$_6$) 8.54 (1H, br, pyrimidine Ar), 7.96-7.90 (2H, br, 2×Ar), 7.48-7.32 (6H, br, 6×Ar), 7.06 (1H, br d, J 7.0, Ar), 5.17 (2H, br, s, OCH$_2$), 4.17 (2H, br q, J 6.5, CO$_2$CH$_2$), 1.27 (3H, br, t, J 6.5, CO$_2$CH$_2$CH$_3$).

REFERENCE EXAMPLE 6

Preparation of Intermediates (22) in Scheme 6

Ethyl 2-(3-benzyloxyphenyl)-4-(morpholin-4-yl) pyrimidine carboxylate (I3)

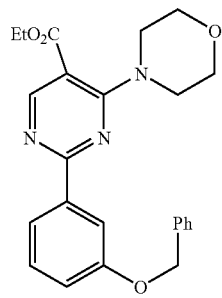

I3

A solution of compound H3 (225 mg, 0.64 mmol) in POCl₃ (2 ml) containing N, N-dimethylaniline (1.1 eq, 0.71 mmol, 0.09 ml) was stirred at 110° C. for 18 h. The POCl₃ was removed in vacuo and the residue azeotroped with toluene (5 ml), re-dissolved in CHCl₃ (5 ml) and poured into ice. The organic layer was separated, washed with water, dried (MgSO₄) and concentrated in vacuo. The crude product was dissolved in dioxane (2 ml) and treated with DIPEA (2 eq, 1.28 mmol, 0.22 ml) and morpholine (5 eq, 3.21 mmol, 0.28 ml) and heated at 80° C. for 4 h. The dioxane was evaporated in vacuo, and the residue partitioned between H₂O (5 ml) and CHCl₃ (5 ml). The organic layer was separated and the aqueous layer further extracted with CHCl₃ (2×2 ml). The combined extracts were dried (Na₂SO₄) and concentrated in vacuo. Purification by column chromatography (hexane-EtOAc, 3:1) gave the product (196 mg, 73% for two steps) as a colourless solid; $\delta_H$ (250 MHz, CDCl₃) 8.79 (1H, s, pyrimidine Ar), 7.96-7.92 (2H, m, 2×Ar), 7.42-7.23 (6H, m, 6× Ar), 7.06-7.02 (1H, m, Ar), 5.09 (2H, s, OCH₂), 4.30 (2H, q, J 7.0, CO₂CH₂), 3.76-3.72 (4H, m, 2× morpholine CH₂), 3.65-3.60 (4H, m, 2× morpholine CH₂), 1.32 (3H, t, J 7.0, CO₂CH₂CH₃).

REFERENCE EXAMPLE 7

Preparation of Intermediates (21) in Scheme 6

2-(3-benzyloxyphenyl)-4-(morpholin-4-yl)pyrimidine carboxylic acid (J3)

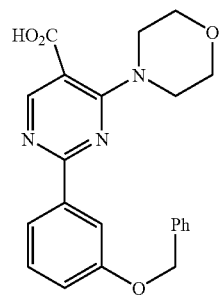

J3

A solution of compound I3 (94 mg) in THF-MeOH-water (5:2:2, 1.5 ml) was treated with lithium hydroxide (5 eq, 1.79 mmol, 75 mg) and stirred at 100° C. for 1.5 h. After this time it was cooled and carefully acidified with 2M HCl, causing precipitation of the product (51 mg) as a yellow solid; $\delta_H$ (250 MHz, DMSO-d₆) 8.63 (1H, s, pyrimidine Ar), 7.97-7.93 (2H, s, 2×Ar), 7.55-7.30 (6H, m, 6× Ar), 7.19-7.15 (1H, m, Ar), 5.20 (2H, s, OCH₂), 3.68-3.65 (8H, m, 4× morpholine CH₂).

REFERENCE EXAMPLE 8

Preparation of Intermediates (27) in Scheme 7

2-chloro-4-(morpholin-4-yl)-5-nitropyrimidine (K3)

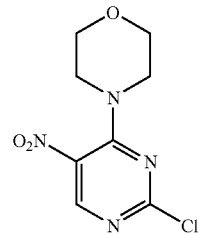

K3

A solution of the dichloropyrimidine (1.00 g, 5.16 mmol) in acetone (10 ml) at 0° C. containing Na₂CO₃ (1.0 eq, 5.16 mmol, 546 mg) was treated dropwise with a solution of morpholine (1.0 eq, 5.16 mmol, 0.45 ml) in acetone (3 ml) and stirred for 1 h at 0° C. Tlc (DCM-hexane, 4:2) showed completion of the reaction to give two products. The acetone was removed in vacuo and the residue partitioned between water and EtOAc, the organic layer dried (MgSO₄) and evaporated in vacuo. Column chromatography (DCM-EtOAC, 9:1) gave the product (560 mg, 45%) as a pale yellow solid, together with 260 mg (17%) of the disubstituted product also as a yellow solid.

K3: $\delta_H$ (250 MHz, CDCl₃) 8.68 (1H, s, pyrimidine Ar), 3.75-3.71 (4H, m, 2× morpholine CH₂), 3.57-3.53 (4H, m, 2× morpholine CH₂).

REFERENCE EXAMPLE 9

Preparation of Intermediate of Formula (26) in Scheme 7

2-(3-methoxyphenyl)-4-(morpholin-4-yl)-5-nitropyrimidine (L3)

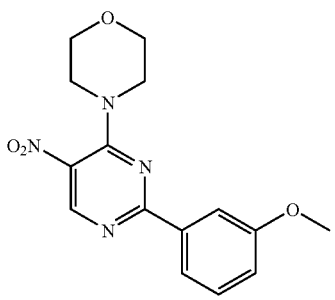

L3

A solution of compound K3 (100 mg, 0.41 mmol) in DME-H₂O-EtOH (7:3:2, 2.5 ml) in a sealable tube was treated with PdCl₂(dppf) (5 mol %, 17 mg), 3-methoxyphenylboronic acid (2.2 eq, 0.90 mmol, 136 mg) and Na₂CO₃ (2.0 eq, 0.82 mmol, 88 mg), sealed and heated at 150° C. in a microwave apparatus for 10 minutes. The solvents were then removed in vacuo and the residue was partitioned between water and CHCl₃, the organic phase separated and dried (MgSO₄) and concentrated in vacuo. Column chromatography (DMC-EtOAc, 95:5) gave the product (50 mg, 39%) as a yellow solid; $\delta_H$ (250 MHz, CDCl₃) 9.07 (1H, s, pyrimidine Ar), 8.04-8.00 (2H, m, 2×Ar), 7.44 (1H, t, J 8.0, Ar), 7.13 (1H, ddd, J 8.0, 2.5, 1.0, Ar), 3.94 (3H, s, OCH₃), 3.90-3.87 (4H, m, 2× morpholine CH₂), 3.77-3.74 (4H, m, 2× morpholine CH₂).

REFERENCE EXAMPLE 10

Preparation of Intermediate (25) in Scheme 7

5-amino-2-(3-methoxyphenyl)-4-(morpholin-4-yl)pyrimidine (M3)

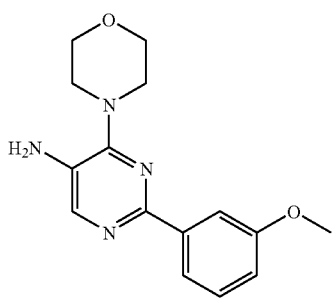

M3

A solution of the nitro compound L3 (31 mg, 0.099 mmol) in EtOH-EtOAc (1:1, 2 ml) containing 10% Pd on carbon (5 mg) was stirred under a balloon of hydrogen gas for 1.5 hours. tlc (DCM-EtOAc, 9:1) then showed completion of the reaction. The mixture was diluted with EtOAc and filtered through a short pad of celite and the solvents evaporated in vacuo to give the amine (25 mg, 89%) as an oil; $\delta_H$ (250 MHz, CDCl₃) 8.03 (1H, s, pyrimidine Ar), 7.87-7.83 (2H, m, Ar), 7.28 (1H, t, J 8.0, Ar), 6.89 (1H, ddd, J 8.0, 2.5, 1.0 Ar), 3.83 (3H, s, OCH₃), 3.80-3.75 (4H, m, 2 x morpholine CH₂), 3.64 (2H, br, NH₂), 3.47-3.43 (4H, m, 2× morpholine CH₂).

EXAMPLE 1

Preparation of Compounds of Formulae (Ib) and (Ic) in Scheme 5

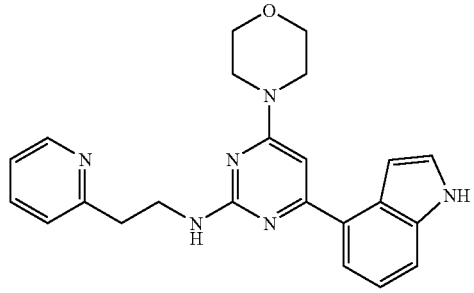

I4

A solution of compound F2 (50 mg, 0.15 mmol), Bedford palladacycle (prepared as described in *Organometallics* 2003, 22, 987; 5 mol %, 5 mg) and indole-4-boronic acid (2.2 eq, 0.34 mmol, 55 mg) in DME (1 ml) in a microwave tube was stirred for 5 minutes. Aqueous sodium carbonate (2M, 2.2 eq, 0.34 mmol, 0.17 ml) was added and the mixture stirred with microwave heating at 150° C. for 30 minutes. After this time it was allowed to cool to room temperature and passed through a short silica column, eluting with CH₂Cl₂-MeOH, 9:1. After concentration of the combined eluents in vacuo, the residue was purified by column chromatography (CHCl3-MeOH, 9:1) to give the product (25 mg, 40%) as a pale brown solid.

$\delta_H$ (500 MHz, CD₃OD) 8.44 (1H, d, J 4.0, pyridine Ar), 7.71 (1H, td, J 7.7, 1.8, pyridine Ar), 7.47 (1H, d, J 8.1, indole Ar), 7.37 (1H, d, J 7.1, pyridine Ar), 7.33 (1H, d, J 7.8, indole Ar), 7.31 (1H, d, J 3.2, indole Ar), 7.23 (1H, dd, J 7.0, 5.5, pyridine Ar), 7.17 (1H, t, J 7.7, indole Ar), 6.79 (1H, br, indole Ar), 6.40 (1H, s, pyrimidine Ar), 3.80 (2H, t, J 6.9, NHCH₂), 3.76-3.74 (4H, m, 2× morpholine CH₂), 3.65-3.63 (4H, m, 2× morpholine CH₂), 3.14 (2H, t, J 6.9, ArCH₂).

Using an analogous method and either indole 4-boronic acid or indole 6-boronic acid, the following further compounds of formulae (Ib) and (Ic) were prepared:

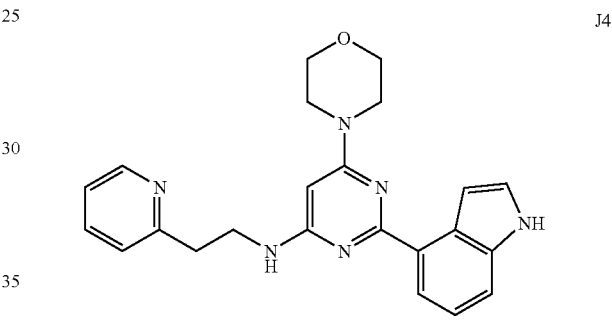

J4

$\delta_H$ (500 MHz, CDCl₃) 8.58 (1H, d, J 4.4, pyridine Ar), 8.46 (1H, s, br, NH), 7.62 (1H, td, J 7.6, 1.8, pyridine Ar), 7.54 (1H, d, J 6.8, pyridine Ar), 7.41 (1H, d, J 8.1, indole Ar), 7.24-7.28 (2H, m, 2× indole Ar), 7.18 (1H, d, J 7.8, indole Ar), 7.16 (1H, dd, J 7.5, 4.9, pyridine Ar), 7.07 (1H, t, J 2.2, indole Ar), 6.22 (1H, s, pyrimidine Ar), 5.23 (1H, t, J 5.5, NH), 3.89-3.87 (4H, m, 2× morpholine CH₂), 3.84-3.81 (2H, m, NHCH₂), 3.80-3.78 (4H, m, 2× morpholine CH₂), 3.12 (2H, t, J 6.6, ArCH₂).

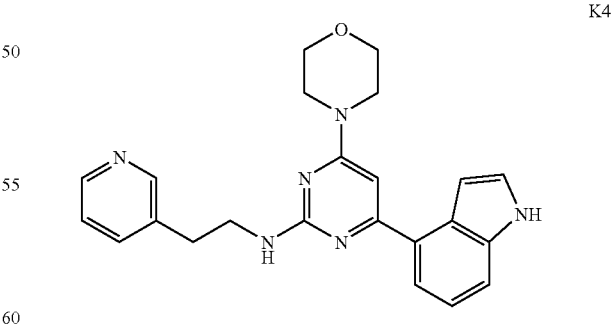

K4

$\delta_H$ (500 MHz, DMSO-d₆) 11.20 (1H, br, NH), 8.47 (1H, d, J 2.0, pyridine Ar), 8.40 (1H, dd, J 4.7, pyridine Ar), 7.67 (1H, dt, J 7.9, 2, pyridine Ar), 7.54 (1H, d, J 7.9 indole Ar), 7.48 (1H, d, J 7.9, indole Ar), 7.40 (1H, t, J 2.8, indole Ar), 7.31 (1H, dd, J 7.6, 4.7, pyridine Ar), 7.15 (1H, t, J 7.6, indole Ar), 7.01 (1H, br, indole Ar), 6.49 (1H, s, br, pyrimidine Ar), 3.70-3.68 (4H, m, 2× morpholine CH$_2$), 3.59-3.57 (6H, m, 2× morpholine CH$_2$, NHCH$_2$), 2.92 (2H, t, J 7.3, ArCH$_2$).

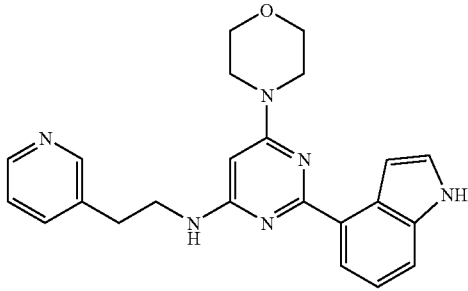

L4

$\delta_H$ (500 MHz, CD$_3$OD) 8.43 (1H, d, J 1.8, pyridine Ar), 8.36 (1H, dd, J 4.7, 1.8, pyridine Ar), 7.75 (1H, dt, J 8.0, 1.9, pyridine Ar), 7.46-7.44 (2H, m, 2× indole Ar), 7.36 (1H, dd, J 7.8, 4.7, pyridine Ar), 7.30 (1H, d, J 3.2, indole Ar), 7.16 (1H, t, J 7.7, indole Ar), 6.89 (1H, dd, J 3.1, 0.6, indole Ar), 6.28 (1H, s, pyrimidine Ar), 3.82-3.80 (4H, m, 2× morpholine CH$_2$), 3.77-3.75 (4H, m, 2× morpholine CH$_2$), 3.71-3.68 (2H, m, NHCH$_2$), 2.99 (2H, t, J 6.9, ArCH$_2$).

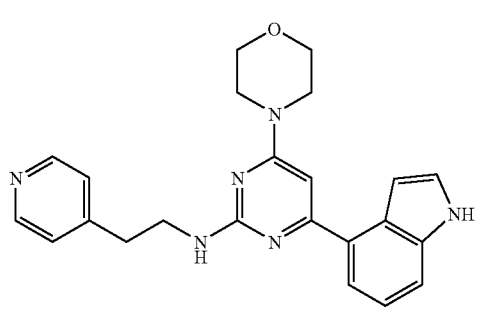

M4

$\delta_H$ (250 MHz, CDCl$_3$) 8.52 (2H, dd, J 4.4, 1.6, 2× pyridine Ar), 8.31 (1H, s, br, NH), 7.55 (1H, d, J 7.3, indole Ar), 7.46 (1H, d, J 8.2, indole Ar), 7.30-7.26 (1H, m, indole Ar), 7.20 (2H, dd, J 4.4, 1.6, 2× pyridine Ar), 7.03 (1H, br, indole Ar), 6.42 (1H, s, indole Ar), 5.31 (1H, s, pyrimidine Ar), 3.81-3.79 (4H, m, 2× morpholine CH$_2$), 3.77 (2H, td, J 7.0, 6.6, NHCH$_2$), 3.66-3.64 (4H, m, 2× morpholine CH$_2$), 2.98 (2H, t, J 7.0, ArCH$_2$).

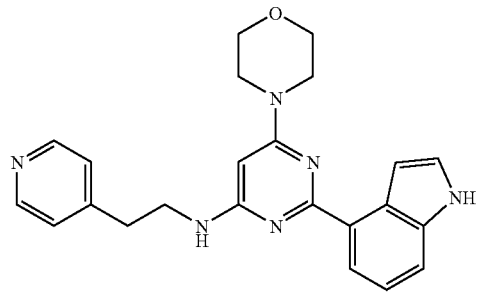

N4

$\delta_H$ (500 MHz, CD$_3$OD) 8.57 (2H, d, J 5.7, 2× pyridine Ar), 7.44 (2H, d, J 7.7, 2× indole Ar), 7.31 (2H, d, J 5.6, 2× pyridine Ar), 7.29 (1H, d, J 3.1, indole Ar), 7.15 (1H, t, J 7.7, indole Ar), 6.89 (1H, d, J 3.1, indole Ar), 6.27 (1H, s, pyrimidine Ar), 3.81-3.79 (4H, m, 2× morpholine CH$_2$), 3.76-3.74 (4H, m, 2× morpholine CH$_2$), 3.69 (2H, t, J 6.9, NHCH$_2$), 2.98 (2H, t, J 6.9, ArCH$_2$).

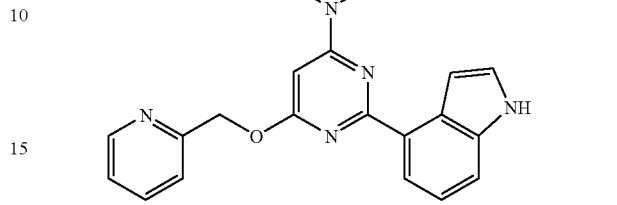

O4

$\delta_H$ (500 MHz, CD$_3$OD) 8.53 (1H, d, J 4.4, pyridine Ar), 7.86 (1H, td, J 7.8, 1.7, pyridine Ar), 7.58-7.55 (2H, m, 1× pyridine Ar, 1× indole Ar), 7.50 (1H, d, J 8.0, indole Ar), 7.36 (1H, dd, J 7.2, 5.2, pyridine Ar), 7.34 (1H, d, J 3.2, indole Ar), 7.19 (1H, t, J 8.0, indole Ar), 6.96 (1H, d, J 3.2, indole Ar), 6.68 (1H, s, pyrimidine Ar), 5.52 (2H, s, OCH$_2$), 3.82-3.80 (4H, m, 2× morpholine CH$_2$), 3.73-3.71 (4H, m, 2× morpholine CH$_2$).

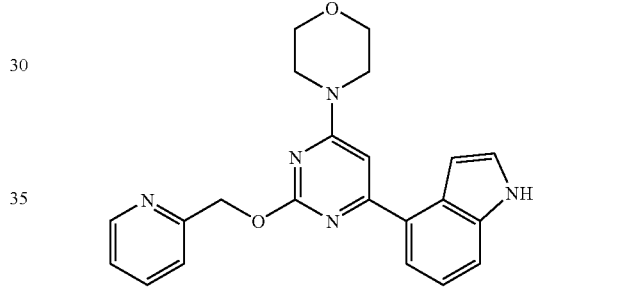

P4

$\delta_H$ (500 MHz, CD$_3$OD) 8.49 (1H, d, J 4.2, pyridine Ar), 7.79 (1H, td, J 7.7, 1.7, pyridine Ar), 7.59 (1H, d, J 7.8, indole Ar), 7.48-7.47 (2H, d, J 7.8, 1× indole Ar, 1× pyridine Ar), 7.31-7.29 (2H, m, 1× indole Ar, 1× pyridine Ar), 7.16 (1H, t, J 7.7, indole Ar), 6.79 (1H, dd, J 3.2, 0.8, indole Ar), 6.73 (1H, s, pyrimidine Ar), 5.51 (2H, s, OCH$_2$), 3.67 (4H, m, 2× morpholine CH$_2$), 3.58-3.56 (4H, m, 2× morpholine CH$_2$).

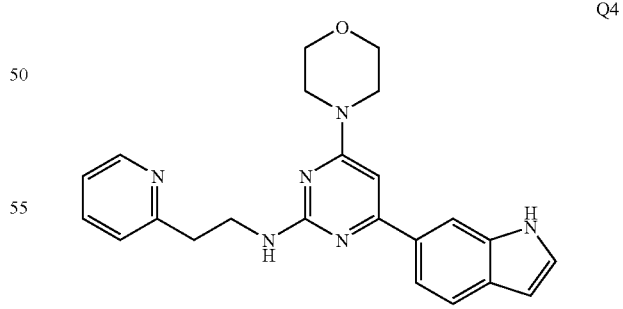

Q4

$\delta_H$ (250 MHz, CDCl$_3$) 9.78 (1H, br, NH), 8.49 (1H, d, J 4.5, pyridine Ar), 8.19 (1H, s, indole Ar), 7.61 (1H, d, J 8.1, indole Ar), 7.58 (1H, d, J 8.1, indole Ar), 7.52 (1H, td, J 7.6, 1.5, pyridine Ar), 7.15 (1H, br, indole Ar), 7.12 (1H, d, J 7.7, pyridine Ar), 7.07 (1H, dd, J 7.1, 4.5, pyridine Ar), 6.47 (1H, s, pyrimidine Ar), 6.29 (1H, br, indole Ar), 3.86-3.83 (2H, m, NHCH$_2$), 3.76-3.74 (4H, m, 2× morpholine CH$_2$), 3.62-3.60 (4H, m, 2× morpholine CH$_2$), 3.09 (2H, t, J 7.0, ArCH$_2$).

pholine CH$_2$), 3.78-3.76 (4H, m 2× morpholine CH$_2$), 3.66 (2H, t, J 7.0, NHCH$_2$), 2.96 (2H, t, J 7.0, ArCH$_2$).

R4

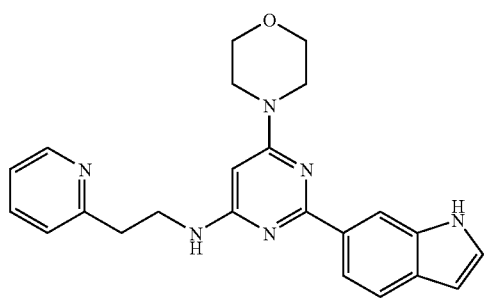

δ$_H$ (500 MHz, CD$_3$OD) 8.45 (1H, d, J 4.5, pyridine Ar), 8.05 (1H, s, indole Ar), 7.70 (1H, td, J 7.8, 1.8, pyridine Ar), 7.61 (1H, dd, J 8.5, 1.2, indole Ar), 7.57 (1H, d, J 8.5 indole Ar), 7.29 (1H, d, J 7.8, pyridine Ar), 7.27 (1H, d, J 3.1, indole Ar), 7.22 (1H, dd, J 6.6, 4.5, pyridine Ar), 6.46 (1H, dd, J 3.1, 0.6, indole Ar), 6.25 (1H, s, pyridine Ar), 3.84-3.82 (4H, m, 2× morpholine CH$_2$), 3.78-3.74 (6H, m, 2× morpholine CH$_2$, NHCH$_2$), 3.09 (2H, t, J 6.9, ArCH$_2$).

U4

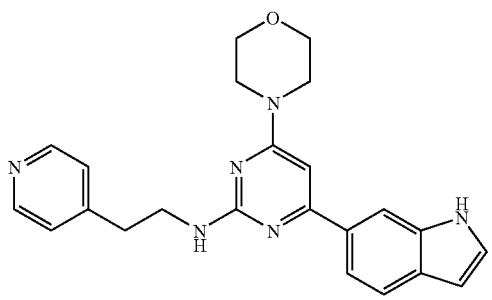

δ$_H$ (500 MHz, CD$_3$OD) 8.44 (2H, d, J 6.0, 2× pyridine Ar), 7.96 (1H, s, indole Ar), 7.64 (1H, d, J 8.5, indole Ar), 7.54 (1H, d, J 8.5, indole Ar), 7.38-7.37 (3H, m, 2× pyridine Ar, 1× indole Ar), 6.52 (1H, s, pyrimidine Ar), 6.51 (1H, dd, J 3.2, 0.7, indole Ar), 3.80-3.74 (10H, 4× morpholine CH$_2$, NHCH$_2$), 3.04 (2H, t, J 6.9, ArCH$_2$).

S4

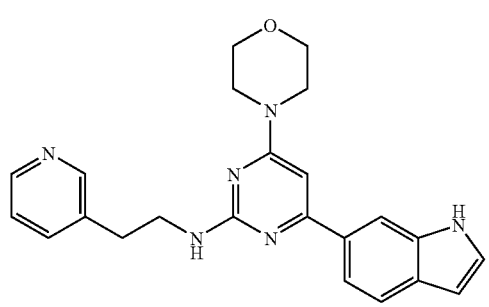

δ$_H$ (500 MHz, CDCl$_3$) 9.22 (1H, br s, NH), 8.49 (1H, s, pyridine Ar), 8.44 (1H, dd, J 4.8, 1.6, pyridine Ar), 8.17 (1H, s, indole Ar), 7.65 (1H, d, J 8.3, indole Ar), 7.61 (1H, d, J 8.3, indole Ar), 7.47 (1H, d, J 7.5, pyridine Ar), 7.20 (1H, t, J 2.9, indole Ar), 7.16 (1H, dd, J 7.5, 4.8, pyridine Ar), 6.52 (1H, br m, indole Ar), 6.35 (1H, s, pyrimidine Ar), 3.79-3.77 (4H, m, 2× morpholine CH$_2$), 3.64-3.60 (6H, m, 2× morpholine CH$_2$, NHCH$_2$), 2.87 (2H, t, J 6.9, ArCH$_2$).

V4

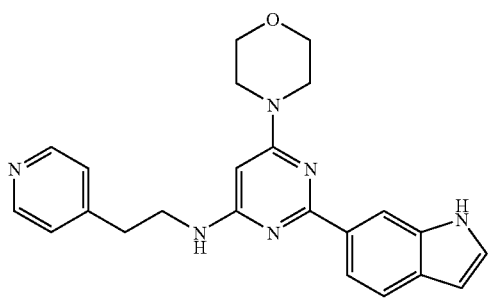

δ$_H$ (500 MHz, CD$_3$OD) 8.43 (2H, dd, J 4.5, 1.5, 2× pyridine Ar), 8.07 (1H, br s, indole Ar), 7.60 (1H, d, J 8.4, 1.5, indole Ar), 7.56 (1H, d, J 8.4, indole Ar), 7.34 (2H, dd, J 4.5, 1.5, 2× pyridine Ar), 7.31 (1H, d, J 3.1, indole Ar), 6.46 (1H, d, J 3.1, indole Ar), 6.28 (1H, s, 2× pyridine Ar), 3.72 (2H, t, J 6.9, NHCH$_2$) 3.84-3.82 (4H, m, 2× morpholine CH$_2$), 3.78-3.76 (4H, m, 2× morpholine CH$_2$) 3.00 (2H, t, J 6.9, ArCH$_2$).

T4

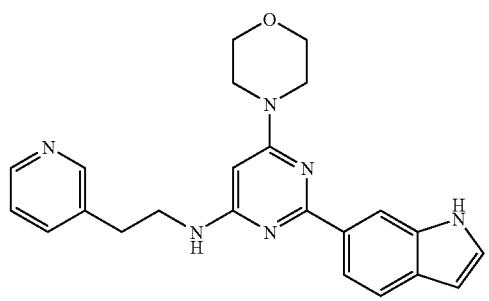

δ$_H$ (500 MHz, CD$_3$OD) 8.40 (1H, S, pyridine Ar), 8.35 (1H, d, J 3.9, pyridine Ar), 8.04 (1H, s, indole Ar), 7.68 (1H, d, J 7.8, pyridine Ar), 7.60 (1H, dd, J 8.3, 1.4, indole Ar) 7.57 (1H, d, J 8.3, indole Ar), 7.32 (1H, dd, J 7.7, 4.9, pyridine Ar), 7.27 (1H, d, J 3.1, indole Ar), 6.46 (1H, dd, J 3.1, 0.7, indole Ar), 6.24 (1H, s, pyrimidine Ar), 3.84-3.82 (4H, m, 2× mor-

W4

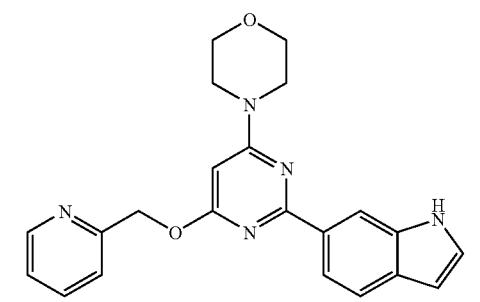

δ$_H$ (500 MHz, CD$_3$OD) 8.53 (1H, d, J 5.5, pyridine Ar), 8.17 (1H, s, indole Ar), 7.86 (1H, td, J 7.7, 1.8, pyridine Ar), 7.72 (1H, dd, J 8.3, 1.6, indole Ar), 7.60 (1H, d, J 8.4, indole Ar), 7.56 (1H, d, J 7.5, pyridine Ar), 7.36 (1H, dd, J 7.5, 5.5, pyridine Ar), 7.33 (1H, d, J 3.3, indole Ar), 6.69 (1H, s, pyrimidine Ar), 6.48 (1H, dd, J 3.1, indole Ar), 5.51 (2H, s, OCH$_2$), 3.84-3.71 (4H, m, 2× morpholine CH$_2$), 3.32-3.32 (4H, m, 2 x morpholine CH$_2$).

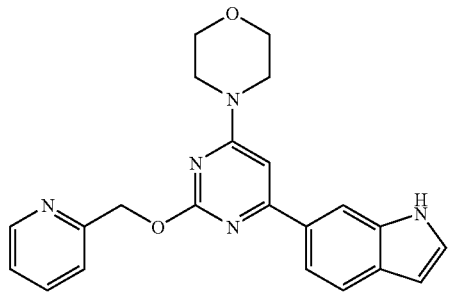

X4

δ$_H$ (500 MHz CDCl$_3$) 8.59 (1H, d, J 4.8, pyridine Ar), 8.39 (1H, br, NH), 8.68 (1H, s, indole Ar), 7.70-7.67 (3H, m, 2× indole Ar, 1× pyridine Ar), 7.59 (1H, d, J 7.9, pyridine Ar), 7.30 (1H, t, J 2.8, indole Ar), 7.19 (1H, dd, J 6.9, 5.4, pyridine Ar), 6.67 (1H, s, pyrimidine Ar), 6.58 (1H, br, indole Ar), 5.64 (2H, s, OCH$_2$), 3.79-3.77 (4H, m, 2× morpholine CH$_2$), 3.69-3.67 (4H, m, 2× morpholine CH$_2$).

EXAMPLE 2

Preparation of Compounds of Formula (Ia) in Scheme 7

2-(3-methoxyphenyl)-4-(morpholin-4-yl)-5-[(pyridin-4-yl)carbonylamino]pyrimidine (N3)

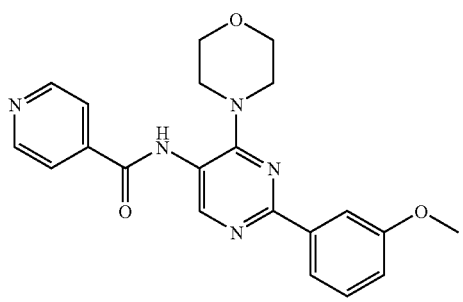

N3

A solution of the amine M3 (25 mg, 0.087 mmol) in CHCl$_3$ (1 ml) at room temperature was treated with diisopropylethylamine (2.5 eq, 0.21 mmol, 0.03 ml) and the acid chloride (2.2 eq, 0.196 mmol, 34 mg) and stirred at room temp for 1 h. tlc (DCM-EtOAc, 9:1) showed incomplete reaction. Further base (0.03 ml) and acid chloride (34 mg) were added and the reaction stirred at room temperature for 18 h. tlc then showed complete conversion. A standard aqueous work up and column chromatography (same eluent) gave the product (16 mg, 47%) as a colourless solid; δ$_H$ (250 MHz, CDCl$_3$) 9.03 (1H, s, pyrimidine Ar), 8.79-8.61 (3H, m, 2× pyridine Ar, NH), 7.94-7.89 (2H, m, Ar), 7.76 (2H, d, J 5.0, pyridine Ar), 7.34 (1H, t, J 8.0, Ar), 6.99 (1H, ddd, J 8.0, 2.5, 1.0, Ar), 3.85 (3H, s, OCH$_3$), 3.81-3.72 (4H, m, 2× morpholine CH$_2$), 3.57-3.53 (4H, m, 2× morpholine CH$_2$).

Using an analogous method, the following further compounds of formula (Ia) were prepared:

2-(3-methoxyphenyl)-4-(morpholin-4-yl)-5-[(pyridin-3-yl)carbonylamino]pyrimidine (O3)

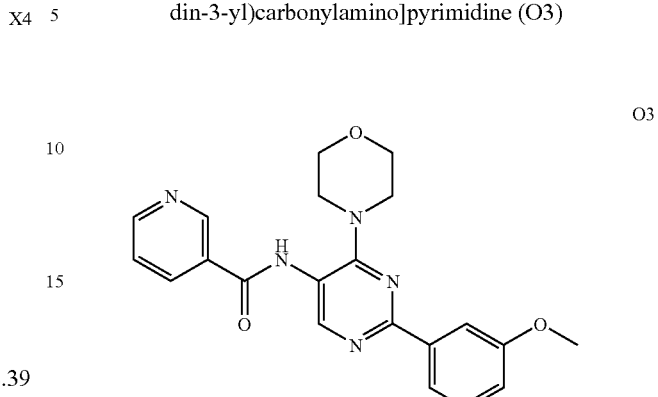

O3

δ$_H$ (250 MHz, CDCl$_3$) 9.17 (1H, br, NH), 9.05 (1H, d, J 2.0, pyrimidine Ar), 8.77 (1H, dd, J 5.0, 1.5, pyridine Ar), 8.21 (1H, dt, J 8.0, 2.0, pyridine Ar), 7.96-7.87 (3H, m, 2× pyridine Ar, 1×Ar), 7.44 (1H, dd, J 8.0, 5.5, Ar), 7.32 (1H, t, J 8.0, Ar), 6.95 (1H, ddd, J 8.0, 2.5, 1.0, Ar), 3.84 (3H, s, OCH$_3$), 3.83-3.79 (4H, m, 2× morpholine CH$_2$), 3.45-3.41 (4H, m, 2× morpholine CH$_2$).

2-(3-methoxyphenyl)-4-(morpholin-4-yl)-5-[(pyridin-3-yl)carbonylamino]pyrimidine (P3)

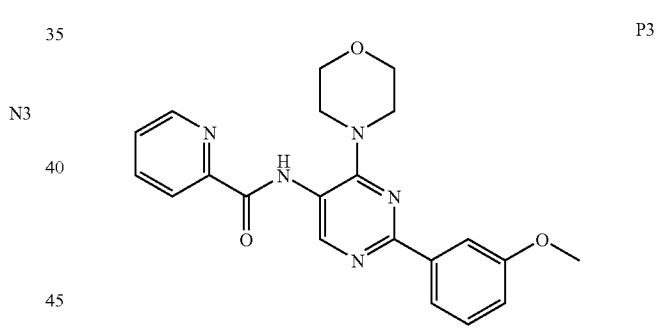

P3

δ$_H$ (250 MHz, CDCl$_3$) 9.96 (1H, br, NH), 9.40 (1H, s, pyrimidine Ar), 8.58 (1H, dq, J 4.5, 1.0, pyridine Ar), 8.24 (1H, dt, J 8.0, 1.0, pyridine Ar), 7.97-7.85 (3H, m, 2× pyridine Ar, 1×Ar), 7.47 1H, ddd, J 8.0, 5.0, 1.0, Ar), 7.31 (1H, t, J 8.0, Ar), 6.94 (1H, ddd, J 8.0, 2.5, 1.0, Ar), 3.90-3.87 (4H, 2× morpholine CH$_2$), 3.85 (3H, s, OCH$_3$), 3.46-3.43 (4H, m, 2× morpholine CH$_2$).

EXAMPLE 3

Biological Testing

Compounds of the invention, prepared as described in the preceding Examples, were submitted to the following series of biological assays:

(i) PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. $IC_{50}$ values were subsequently determined using sigmoidal dose-response curve fit (variable slope). All of the compounds tested had an $IC_{50}$ against PI3K of 50 μM or less. Typically the $IC_{50}$ against PI3K was 5-500 nM.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 hours before reading at 544 nm excitation, 590 nm emission. $EC_{50}$ values were calculated using a sigmoidal dose response curve fit. All the compounds tested had an $EC_{50}$s of 50 uM or less in the range of cell lines utilized.

EXAMPLE 4

Tablet Composition

Tablets, each weighing 0.15 g and containing 25 mg of a compound of the invention were manufactured as follows:

| Composition for 10,000 tablets |
| --- |
| Compound of the invention (250 g) |
| Lactose (800 g) |
| Corn starch (415 g) |
| Talc powder (30 g) |
| Magnesium stearate (5 g) |

The compound of the invention, lactose and half of the corn starch were mixed. The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

EXAMPLE 5

Injectable Formulation

| | |
| --- | --- |
| Compound of the invention | 200 mg |
| Hydrochloric Acid Solution 0.1M or | 4.0 to 7.0 |
| Sodium Hydroxide Solution 0.1M q.s. to pH | |
| Sterile water q.s. to | 10 ml |

The compound of the invention was dissolved in most of the water (35° 40° C.) and the pH adjusted to between 4.0 and 7.0 with the hydrochloric acid or the sodium hydroxide as appropriate. The batch was then made up to volume with water and filtered through a sterile micropore filter into a sterile 10 ml amber glass vial (type 1) and sealed with sterile closures and overseals.

EXAMPLE 6

Intramuscular Injection

| | |
| --- | --- |
| Compound of the invention | 200 mg |
| Benzyl Alcohol | 0.10 g |
| Glycofurol 75 | 1.45 g |
| Water for injection q.s to | 3.00 ml |

The compound of the invention was dissolved in the glycofurol. The benzyl alcohol was then added and dissolved, and water added to 3 ml. The mixture was then filtered through a sterile micropore filter and sealed in sterile 3 ml glass vials (type 1).

EXAMPLE 7

Syrup Formulation

| | |
| --- | --- |
| Compound of invention | 250 mg |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A compound which is a pyrimidine of formula (I):

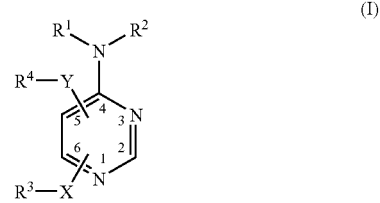

wherein
- —$XR^3$ is bonded at ring position 2 and —$YR^4$ is bonded at ring position 5 or 6, or —$YR^4$ is bonded at ring position 2 and —$XR^3$ is bonded at ring position 6;
- $R^1$ and $R^2$ form, together with the N atom to which they are attached, a morpholine ring which is unsubstituted or substituted;
- X is selected from a direct bond, —O—, —CR'R"— and —NR'— wherein R' and R" are each, independently, H or $C_1$-$C_6$ alkyl;

$R^3$ is an indole group which is unsubstituted or substituted; and either:

(a) Y is selected from —O—$(CH_2)_n$—, —NH—$(CH_2)_n$—, —NHC(O)—$(CH_2)_n$— and —C(O)NH—$(CH_2)_n$— wherein n is 0 or an integer of 1 to 3, and $R^4$ is selected from an unsaturated 5- to 12-membered carbocyclic or heterocyclic group which is unsubstituted or substituted, and a group —$NR^5R^6$ wherein $R^5$ and $R^6$, which are the same or different, are each independently selected from H, $C_1$-$C_6$ alkyl which is unsubstituted or substituted, $C_3$-$C_{10}$ cycloalkyl which is unsubstituted or substituted, —C(O)R, —C(O)N(R)$_2$ and —S(O)$_m$R wherein R and m are as defined above, or $R^5$ and $R^6$ together form, with the nitrogen atom to which they are attached, a saturated 5-, 6- or 7-membered N-containing heterocyclic group which is unsubstituted or substituted;

(b) Y is a direct bond and $R^4$ is selected from an unsaturated 5- to 12-membered carbocyclic or heterocyclic group which is unsubstituted or substituted, and a group —$NR^5R^6$ wherein $R^5$ and $R^6$, which are the same or different, are each independently selected from H, $C_1$-$C_6$ alkyl which is unsubstituted or substituted, $C_3$-$C_{10}$ cycloalkyl which is unsubstituted or substituted, —C(O)R, —C(O)N(R)$_2$ and —S(O)$_m$R wherein R and m are as defined above;

or a pharmaceutically acceptable salt thereof.

2. A compound according to claim 1 wherein the pyrimidine is of formula (Ia):

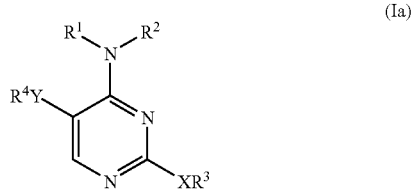

in which $R^1$, $R^2$, $R^3$, $R^5$, Y and X are as defined in claim 1.

3. A compound according to claim 1 wherein the pyrimidine is of formula (Ib):

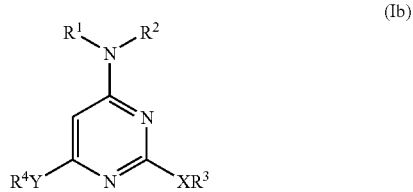

in which $R^1$, $R^2$, $R^3$, $R^4$, Y and X are as defined in claim 1.

4. A compound according to claim 1 wherein the pyrimidine is of formula (Ic):

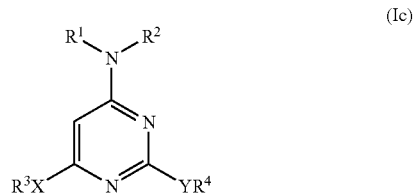

in which $R^1$, $R^2$, $R^3$, $R^4$, Y and X are as defined in claim 1.

5. A compound according to claim 1 wherein —X is a direct bond.

6. A compound according to claim 1 which is selected from:

6-(indol-4-yl)-4-(morpholin-4-yl)-2-[(2-(pyridin-2-yl)ethylamino]pyrimidine;
2-(indol-4-yl)-4-(morpholin-4-yl)-6-[(2-(pyridin-2-yl)ethylamino]pyrimidine;
6-(indol-4-yl)-4-(morpholin-4-yl)-2-[(2-(pyridin-3-yl)ethylamino]pyrimidine;
2-(indol-4-yl)-4-(morpholin-4-yl)-6-[(2-(pyridin-3-yl)ethylamino]pyrimidine;
6-(indol-4-yl)-4-(morpholin-4-yl)-2-[(2-(pyridin-4-yl)ethylamino]pyrimidine;
2-(indol-4-yl)-4-(morpholin-4-yl)-6-[(2-(pyridin-4-yl)ethylamino]pyrimidine;
2-(indol-4-yl)-4-(morpholin-4-yl)-6-(pyridin-2-ylmethyloxy)pyrimidine;
6-(indol-4-yl)-4-(morpholin-4-yl)-2-(pyridin-2-ylmethyloxy)pyrimidine;
6-(indol-6-yl)-4-(morpholin-4-yl)-2-[(2-(pyridin-2-yl)ethylamino]pyrimidine;
2-(indol-6-yl)-4-(morpholin-4-yl)-6-[(2-(pyridin-2-yl)ethylamino]pyrimidine;
6-(indol-6-yl)-4-(morpholin-4-yl)-2-[(2-(pyridin-3-yl)ethylamino]pyrimidine;
2-(indol-6-yl)-4-(morpholin-4-yl)-6-[(2-(pyridin-3-yl)ethylamino]pyrimidine;
6-(indol-6-yl)-4-(morpholin-4-yl)-2-[(2-(pyridin-4-yl)ethyl amino]pyrimidine;
2-(indol-6-yl)-4-(morpholin-4-yl)-6-[(2-(pyridin-4-yl)ethylamino]pyrimidine;
2-(indol-6-yl)-4-(morpholin-4-yl)-6-(pyridin-2-ylmethyloxy)pyrimidine;
6-(indol-6-yl)-4-(morpholin-4-yl)-2-(pyridin-2-ylmethyloxy)pyrimidine;

and the pharmaceutically acceptable salts thereof.

7. A pharmaceutical composition which comprises a pharmaceutically acceptable carrier or diluent and, as an active ingredient, a compound as defined in claim 1.

* * * * *